United States Patent
Egli et al.

(10) Patent No.: US 10,550,171 B2
(45) Date of Patent: Feb. 4, 2020

(54) IMMUNOMODULATORY PEPTIDES AND METHODS OF USE THEREOF

(71) Applicant: THE GOVERNORS OF THE UNIVERSITY OF ALBERTA, Edmonton (CA)

(72) Inventors: Adrian Egli, Edmonton (CA); Deanna Michelle Santer, Edmonton (CA); Aviad Yaagov Levin, Edmonton (CA); Bradley Scott Thomas, Edmonton (CA); Khaled Hassan Sayed Barakat, Edmonton (CA); Michael A. Joyce, Edmonton (CA); Daire Thomas O'Shea, Edmonton (CA); Rakesh Kumar Bhat, Edmonton (CA); Michael Houghton, Edmonton (CA); D. Lorne J. Tyrrell, Edmonton (CA); Atul Humar, Edmonton (CA); Deepali Kumar, Edmonton (CA)

(73) Assignee: The Governors of the University of Alberta, Alberta (CA)

(*) Notice: Subject to any disclaimer, the term of this patent is extended or adjusted under 35 U.S.C. 154(b) by 916 days.

(21) Appl. No.: 14/443,630

(22) PCT Filed: Nov. 21, 2013

(86) PCT No.: PCT/IB2013/060289
§ 371 (c)(1),
(2) Date: May 18, 2015

(87) PCT Pub. No.: WO2014/080350
PCT Pub. Date: May 30, 2014

(65) Prior Publication Data
US 2015/0307590 A1    Oct. 29, 2015

Related U.S. Application Data

(60) Provisional application No. 61/728,996, filed on Nov. 21, 2012.

(51) Int. Cl.
| | |
|---|---|
| *C07K 14/00* | (2006.01) |
| *C07K 14/715* | (2006.01) |
| *C07K 16/28* | (2006.01) |
| *A61K 39/12* | (2006.01) |
| *A61K 39/39* | (2006.01) |
| *A61K 39/145* | (2006.01) |
| *A61K 39/245* | (2006.01) |
| *C07K 14/57* | (2006.01) |
| *C12N 7/00* | (2006.01) |
| *A61K 39/00* | (2006.01) |

(52) U.S. Cl.
CPC ........ *C07K 14/7155* (2013.01); *A61K 39/145* (2013.01); *A61K 39/245* (2013.01); *A61K 39/39* (2013.01); *C07K 14/57* (2013.01); *C07K 16/2866* (2013.01); *C12N 7/00* (2013.01); *A61K 2039/55516* (2013.01); *C07K 2317/76* (2013.01); *C12N 2710/16134* (2013.01); *C12N 2760/16034* (2013.01)

(58) Field of Classification Search
None
See application file for complete search history.

(56) References Cited

U.S. PATENT DOCUMENTS

| | | | | |
|---|---|---|---|---|
| 2008/0125367 A1* | 5/2008 | Glenn | .................. | A61K 38/162 435/5 |
| 2008/0220017 A1* | 9/2008 | Cham | .................. | A61M 1/3486 424/204.1 |

FOREIGN PATENT DOCUMENTS

| | | |
|---|---|---|
| JP | 2013136530 | 7/2013 |
| WO | WO 2002/092762 | 11/2002 |
| WO | WO 2002/092762 A2 | 11/2002 |
| WO | WO 2006/012644 A2 | 2/2006 |
| WO | WO 2010/045261 | 4/2010 |
| WO | WO 2010/059984 | 5/2010 |
| WO | WO 2011/098644 | 8/2011 |

OTHER PUBLICATIONS

Egli et al., PLOS Pathog. 10(12):e1004556 (Year: 2014).*
Alaoui-Ismaili et al., Cytokine Growth Factor Rev. 20(5-6):501-7 (Year: 2009).*
Egli et al., The Journal of Infectious Diseases, vol. 210, Issue 5, pp. 717-727 (Year: 2014).*
Ank, et al.; "An Important Role for Type III Interferon (IFN-I/IL-28) in TLR-Induced Antiviral Activity"; J. Immunol.; vol. 180, pp. 2474-2485 (2008).
Chi et al.; "Alpha and lambda interferon together mediate suppression of CD4 T cells induced by respiratory syncytial virus"; Journal of Virology; vol. 80, No. 10, pp. 5032-5040 (2006).
Dill, et al.; "Interferon-Induced Gene Expression Is a Stronger Predictor of Treatment Response Than IL28B Genotype in Patients With Hepatitis C"; Gastroenterology; vol. 140, pp. 1021-1031 (2011).
GenBank Database, Accession ADO12077.1, IFN-lambda1, partial [*Homosapiens*] (Oct. 6, 2010).
Hillyer, et al.; "Expression profiles of human interferon-alpha and interferon-lambda subtypes are ligand- and cell-dependent"; Immunology and Cell Biology; vol. 90, pp. 774-783 (2012).

(Continued)

*Primary Examiner* — Daniel E Kolker
*Assistant Examiner* — Jegatheesan Seharaseyon
(74) *Attorney, Agent, or Firm* — Bozicevic, Field & Francis LLP; Paula A. Borden

(57) ABSTRACT

The present disclosure provides peptides that modulate an immune response in an individual. The present disclosure provides peptides that modulate cellular responses in vitro. The present disclosure provides compositions comprising the peptides. The peptides and compositions are useful in methods of modulating an immune response in an individual, which methods are also provided.

15 Claims, 15 Drawing Sheets

Specification includes a Sequence Listing.

(56) References Cited

OTHER PUBLICATIONS

Thomas, et al.; "HCV Infection Induces a Unique Hepatic Innate Immune Response Associated With Robust Production of Type III Interferons"; Gastroenterology; vol. 142, pp. 978-988 (2012).

* cited by examiner

Figure 3

IL-29
*Homo sapiens*
GenBank NP_742152
200 aa

```
  1 maaawtvvlv tlvlglavag pvptskpttt gkgchigrfk slspqelasf kkardalees
 61 lklknwscss pvfpgnwdlr llqvrerpva leaelaltlk vleaaagpal edvldqplht
121 lhhilsqlqa ciqpqptagp rprgrlhhwl hrlqeapkke sagcleasvt fnlfrlltrd
181 lkyvadgnlc lrtsthpest (SEQ ID NO:1)
```

Figure 4

IL-28A
*Homo sapiens*
GenBank NP_742150
200 aa

```
  1 mkldmtgdct pvlvlmaavl tvtgavpvar lhgalpdarg chiaqfksls pqelqafkra
 61 kdaleeslll kdcrchsrlf prtwdlrqlq vrerpmalea elaltlkvle atadtdpalv
121 dvldqplhtl hhilsqfrac iqpqptagpr trgrlhhwly rlqeapkkes pgcleasvtf
181 nlfrlltrdl ncvasgdlcv (SEQ ID NO:2)
```

Figure 5

IL-28B
*Homo sapiens*
GenBank NP_742151
196 aa

```
  1 mtgdcmpvlv lmaavltvtg avpvarlrga lpdargchia qfkslspqel qafkrakdal
 61 eesllikdck crsrlfprtw dlrqlqvrer pvaleaelal tlkvleatad tdpalgdvld
121 qplhtlhhil sqlraciqpq ptagprtrgr lhhwlhrlqe apkkespgcl easvtfnlfr
181 lltrdlncva sgdlcv (SEQ ID NO:3)
```

Figure 6

IL-28 R α subunit
*Homo sapiens*
GenBank NP_734464
520 aa; isoform 1

```
  1 magperwgpl llcllqaapg rprlappqnv tllsqnfsvy ltwlpglgnp qdvtyfvayq
 61 ssptrrrwre veecagtkel lcsmmclkkq dlynkfkgrv rtvspssksp wveseyldyl
121 fevepappvl vltqteeils anatyqlppc mppldlkyev afwkegagnk tlfpvtphgq
181 pvqitlqpaa sehhclsart iytfsvpkys kfskptcfll evpeanwafl vlpsllilll
241 viaaggviwk tlmgnpwfqr akmpraldfs ghthpvatfq psrpesvndl flcpqkeltr
301 gvrptprvra patqqtrwkk dlaedeeeed eedtedgvsf qpyieppsfl gqehqapghs
361 eaggvdsgrp raplvpsegs sawdssdrsw astvdsswdr agssgylaek gpgqgpggdg
421 hqeslpppef skdsgfleel pednlsswat wgtlppepnl vpggppvslq tltfcwessp
481 eeeearese iedsdagswg aestqrtedr grtlghymar (SEQ ID NO:4)
```

Figure 12

Amino acid sequence for antibody production against IL-28R1.

| code | sequence | antigenic score | origin |
|---|---|---|---|
| Peptide 1 | GPLLLCLLQAAPGRPRLAPPQNVTLLSQNFSVYLTWLP | 1.247; 1.13 | new target |
| Peptide 2 | DVTYFVAYQSSPTRRRWREVEECAGTKELLCSMMCLKNQ | 1.165; 1.141 | covers peptide 8 and 9 |
| Peptide 3 | VRTVSPSSKSPWVESVLDYLPEVEPAPFVLVLTQ | 1.091; 1.308 | covers peptide 10 |
| Peptide 4 | SANATYQLPPCMPPLDLKYEVAFW | 1.125 | covers peptide 11 |
| Peptide 5 | LFPVTPHGQPVQITLQPAASEHHCLSARTYTFSVFKYSKT | 1.124 | covers peptide 12 |

Figure 13
*Homo sapiens*
IFN-λ4

```
  1 mrpsvwaava aglwvlctvi aaaprrclls hyrsleprtl aaakalrdry eeealswgqr
 61 ncsfrprrdp prpsscarlr hvargiadaq avlsglhrse llpgagpile llaaagrdva
121 aclelarpgs srkvpgaqkr rhkprradsp rcrkasvvfn llrlltwelr laahsgpcl  (SEQ ID NO:34)
```

Figure 18

IL-10R2 (IL-10 β subunit)
*Homo sapiens*

MAWSLGSWLGGCLLVSALGMVPPPENVRMNSVNFKNILQWESPAFAKGNLTFTAQYLSYRIFQDKCMNTTLTECDFSSLSKYGDHTLRVRAEFADEHS
DWVNITFCPVDDTIIGPPGMQVEVLADSLHMRFLAPKIENEYETWTMKNVYNSWTYNVQYWKNGTDEKFQITPQYDFEVLRNLEPWTTYCVQVRGFLP
DRNKAGEWSEPVCEQTTHDETVPSWMVAVILMASVFMVCLALLGCFALLWCVYKKTKYAFSPRNSLPQHLKEFLGHPHHNTLLFFSFPLSDENDVFDK
LSVIAEDSESGKQNPGDSCSLGTPPGQGPQS (SEQ ID NO:35)

IMMUNOMODULATORY PEPTIDES AND METHODS OF USE THEREOF

CROSS-REFERENCE

This application claims the benefit of U.S. Provisional Patent Application No. 61/728,996 filed Nov. 21, 2012, which application is incorporated herein by reference in its entirety.

INCORPORATION BY REFERENCE OF SEQUENCE LISTING PROVIDED AS A TEXT FILE

A Sequence Listing is provided herewith as a text file, "UALB-010WO SeqList_ST25" created on Nov. 19, 2013 and having a size of 45 KB. The contents of the text file are incorporated by reference herein in their entirety.

INTRODUCTION

In immunosuppressed individuals, viral infections are common, and can cause significant morbidity, reduced long-term graft survival, and mortality. Infections with cytomegalovirus (CMV) and influenza virus strains are associated with high disease burden in various patients.

An efficient immune response and protective vaccine response with effective T- and B-cell proliferation and antibody production involves complex interactions between aspects of the innate and adaptive immune systems. However, under conditions of prolonged immunosuppression, immune responses are often inadequate.

There is a need in the art for compositions and methods for modulating an immune response, e.g., in response to vaccination and/or infection.

SUMMARY

The present disclosure provides peptides that modulate an immune response in an individual. The present disclosure provides peptides that modulate cellular responses in vitro. The present disclosure provides compositions comprising the peptides. The peptides and compositions are useful in methods of modulating an immune response in an individual, which methods are also provided.

FEATURES

The present disclosure provides isolated peptide having a length of up to about 100 amino acids, wherein the peptide comprises an amino acid sequence selected from:

a) ELX$_1$X$_2$FKX$_3$AX$_4$DALEESLX$_5$L (SEQ ID NO:10), where X$_1$ is A or Q; X$_2$ is S or A; X$_3$ is K or R; X$_4$ is R or K; and X$_5$ is K or L;

b) ASVTFNLFRLLTRDLX$_1$X$_2$ (SEQ ID NO: 13), where X$_1$ is K or N; and X$_2$ is Y or C;

c) X$_1$LKX$_2$X$_3$X$_4$CX$_5$X$_6$X$_7$FPX$_8$X$_9$WDLRX$_{10}$ (SEQ ID NO: 14), where X$_1$ is L or K; X$_2$ is D or N; X$_3$ is C or W; X$_4$ is K, R, or S; X$_5$ is R, H, or S; X$_6$ is R or P; X$_7$ is L or V; X$_8$ is R or G; X$_9$ is T or N; and X$_{10}$ is Q or L.

In some embodiments, a peptide of the present disclosure comprises the amino acid ELX$_1$X$_2$FKX$_3$AX$_4$DALEESLX$_5$L (SEQ ID NO: 10), where X$_1$ is A or Q; X$_2$ is S or A; X$_3$ is K or R; X$_4$ is R or K; and X$_5$ is K or L.

In some embodiments, a peptide of the present disclosure comprises the amino acid ASVTFNLFRLLTRDLX$_1$X$_2$ (SEQ ID NO:13), where X$_1$ is K or N; and X$_2$ is Y or C.

In some embodiments, a peptide of the present disclosure comprises the amino acid X$_1$LKX$_2$X$_3$X$_4$CX$_5$SX$_6$X$_7$FPX$_5$X$_9$WDLRX$_{10}$ (SEQ ID NO:14), where X$_1$ is L or K; X$_2$ is D or N; X$_3$ is C or W; X$_4$ is K, R, or S; X$_5$ is R, H, or S; X$_6$ is R or P; X$_7$ is L or V; X$_5$ is R or G; X$_9$ is T or N; and X$_{10}$ is Q or L.

In any of the above-described embodiments, a peptide of the present disclosure can have a length of from about 14 amino acids to about 20 amino acids.

In any of the above-described embodiments, a peptide of the present disclosure can comprise a non-peptide isosteric linkage.

In any of the above-described embodiments, a peptide of the present disclosure can comprise at least one non-encoded amino acid. For example, in some cases, the non-encoded amino acid is a D-amino acid.

The present disclosure provides a composition comprising: a) a peptide of present disclosure (e.g., as described above and/or hereinbelow); and b) a pharmaceutically acceptable excipient.

In some embodiments, a composition of the present disclosure further comprises a pathogen or a pathogen component. For example, the pathogen can be a live attenuated virus, an inactivated virus, a split virus, a virus subunit, or a nucleic acid comprising a nucleotide sequence encoding a virus subunit. As an example, the virus can be an influenza virus. As another example, the virus can be is a member of Herpesviridae.

In some embodiments, a composition of the present disclosure comprises two or more different peptides of present disclosure (e.g., as described above and/or hereinbelow).

For example, in some embodiments, the two or more peptides comprise:

a) a peptide that is derived from an IFN-λ polypeptide, wherein the peptide inhibits binding of an IFN-λ polypeptide to an IL-28 receptor (IL-28R); and b) a peptide that is derived from an IL-28R, wherein the peptide inhibits binding of an IFN-λ polypeptide to an IL-28R. IL-28R is a heterodimeric protein that includes an IL-28-R1 polypeptide (also referred to as "IL-28R-alpha subunit") and an IL-10-R2 polypeptide (also referred to as an "IL-10R beta subunit"). In some cases, a peptide that is derived from an IL-28R is derived from an IL-28-R1 polypeptide. In some cases, a peptide that is derived from an IL-28R is derived from an IL-10-R2 polypeptide.

The present disclosure provides a method of increasing an immune response in an individual, the method comprising administering to an individual in need thereof an effective amount of a peptide of the present disclosure, or a composition of the present disclosure. In some cases, the individual is a human. In some cases, the individual is immunocompromised. In carrying out a method of the present disclosure, the administering can be via intramuscular injection, intradermal injection, subcutaneous injection, or via inhalation.

The present disclosure provides a method of modulating a cellular response in vitro or ex vivo, the method comprising contacting a cell or a cell population in vitro or ex vivo with a peptide of the present disclosure, wherein said contacting modulates a cellular response. The cellular response can comprise proliferation, cytokine production, or immunoglobulin production.

The present disclosure provides a method of modulating an immune response in an individual, the method comprising administering to an individual in need thereof an effective amount of an agent that inhibits binding of an IFN-λ polypeptide to an IL-28R. In some cases, the agent is a peptide of the present disclosure. In other cases, the agent is an antibody specific for IL-28R.

BRIEF DESCRIPTION OF THE DRAWINGS

FIG. 3 depicts an amino acid sequence of human IL-29 (SEQ ID NO: 1). IL-29 is also referred to as "IFN-λ1."

FIG. 4 depicts an amino acid sequence of human IL-28A (SEQ ID NO:2). IL-28A is also referred to as "IFN-λ2."

FIG. 5 depicts an amino acid sequence of human IL-28B (SEQ ID NO:3). IL-28B is also referred to as "IFN-λ3."

FIG. 6 depicts an amino acid sequence of human IL-28R alpha subunit (SEQ ID NO:4). IL-28R alpha subunit is also referred to as "IL-28R1."

FIG. 12 depicts amino acid sequences of peptides used to generate antibodies to IL-28R. (Peptide 1: SEQ ID NO:5; Peptide 2: SEQ ID NO:6; Peptide 3: SEQ ID NO:7; Peptide 4: SEQ ID NO:8; Peptide 5: SEQ ID NO:9).

FIG. 13 depicts an amino acid sequence of human IFN-λ4 (SEQ ID NO:34).

FIG. 18 depicts an amino acid sequence of human IL-10 receptor (IL-10R1) (SEQ ID NO:35).

DEFINITIONS

Figure 1:
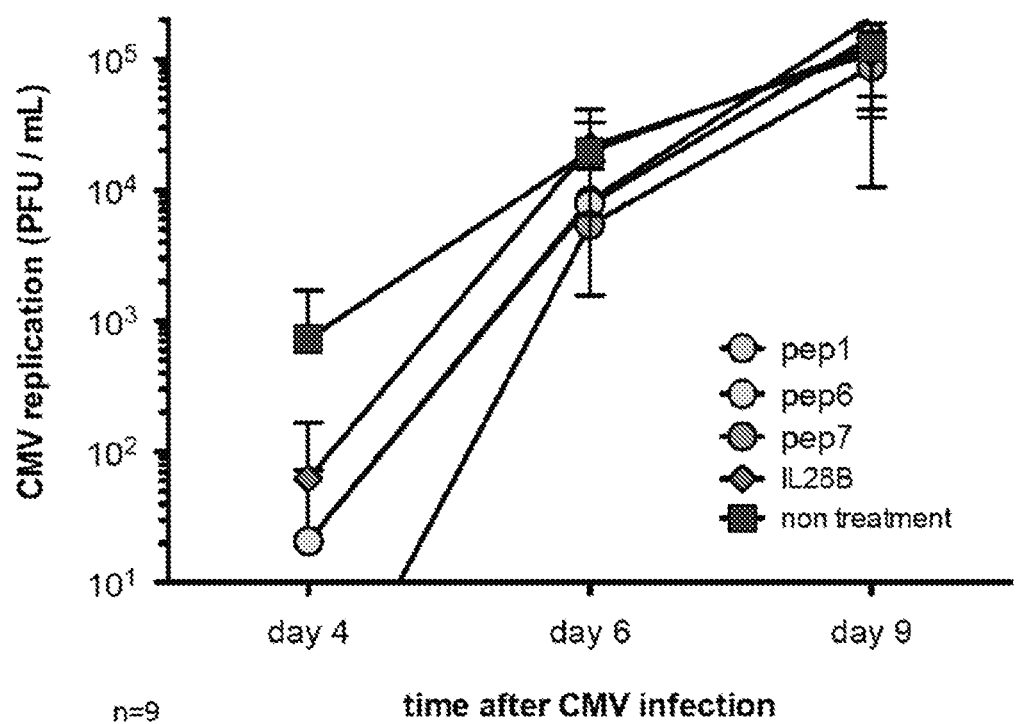
FIG. 1 depicts antiviral effects of peptides on cytomegalovirus (CMV) replication.

"IL-29" (also referred to as "interferon-lambda-1" (IFN-λ1) or "zcyto21") encompasses a polypeptide of about 200 amino acids in length, which binds a heterodimeric IL-28 receptor (IL-28R) complex. Amino acid sequences of IL-29, including human IL-29, are known. See, e.g., GenBank Accession No. NP_724152; and the amino acid sequence depicted in FIG. 3.

"IL-28A" (also referred to as "interferon-lambda-2" (IFN-λ2) or "zcyto20") encompasses a polypeptide of about 200 amino acids in length, which binds a heterodimeric IL-28R complex. Amino acid sequences of IL-28A, including human IL-28A, are known. See, e.g., GenBank Accession No. NP_742150; and the amino acid sequence depicted in FIG. 4.

"IL-28B" (also referred to as "interferon-lambda-3" (IFN-λ3) or "zcyto22") encompasses a polypeptide of about 196 amino acids in length, which binds a heterodimeric IL-28R complex. Amino acid sequences of IL-28B, including human IL-28B, are known. See, e.g. GenBank Accession No. NP_742151; and the amino acid sequence depicted in FIG. 5.

"Interferon-lambda-4" (IFN-λ4) encompasses a polypeptide of about 325 amino acids in length, which binds a heterodimeric IL-28R complex. Amino acid sequences of IFN-λ4, including human IFN-λ4, are known. See, e.g. GenBank Accession No. BC001903; and the amino acid sequence depicted in FIG. 13.

IL-29, IL28A, IL28B, and IFN-λ4 bind to the IL-28 receptor (IL-28R). IL-28R is a complex comprising IL-28R1 (also referred to as "IL-28R-α") and IL-10R2 (also referred to as "IL-10Rβ"). Exemplary amino acid sequences of IL-28R1 and IL-10R2 are depicted in FIGS. 6 and 18, respectively.

"Isolated" refers to a peptide of interest that, if naturally occurring, is in an environment different from that in which it may naturally occur. "Isolated" is meant to include peptides that are within samples that are substantially enriched for the peptide of interest and/or in which the peptide of interest is partially or substantially purified. Where the peptide is not naturally occurring, "isolated" indicates the peptide has been separated from an environment in which it was made by either synthetic or recombinant means.

"Substantially pure" indicates that an entity (e.g., a subject peptide) makes up greater than about 50% of the total content of the composition (e.g., total protein of the composition), or greater than about 80% of the total protein content. For example, a "substantially pure" peptide refers to compositions in which at least 80%, at least 85%, at least 90% or more of the total composition is the peptide (e.g. 95%, 98%, 99%, greater than 99% of the total protein). The peptide can make up greater than about 90%, greater than about 95%, greater than 98%, or greater than 99%, of the total protein in the composition.

In some embodiments, a peptide (or a mixture of peptides) is substantially pure when the peptide (or mixture of peptide) is at least 60% or at least 75% by weight free from organic molecules with which it is naturally associated or with which it is associated during production. In some embodiments, the peptide (or mixture of peptide) is at least 60%, at least 75%, at least 80%, at least 85%, at least 90%, at least 95%, or at least 99%, by weight, pure. For example, in some embodiments, an immunomodulatory peptide (or a mixture of immunomodulatory peptides) is substantially pure when the immunomodulatory peptide (or mixture of immunomodulatory peptides) is at least 60% or at least 75% by weight free from organic molecules with which the peptide(s) is naturally associated or with which it is associated during production. In some embodiments, the immunomodulatory peptide (or mixture of immunomodulatory peptides) is at least 60%, at least 75%, at least 80%, at least 85%, at least 90%, at least 95%, or at least 99%, by weight, pure.

The terms "individual," "host," "subject," and "patient" are used interchangeably herein, and refer to a mammal, including, but not limited to, non-human primates (e.g., simians), and humans.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an immunomodulatory peptide" includes a plurality of such peptides and reference to "the Th2 cytokine" includes reference to one or more Th2 cytokines and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides peptides that modulate an immune response in an individual. The present disclosure provides peptides that modulate cellular responses in vitro. The present disclosure provides compositions comprising the peptides. The peptides and compositions are useful in methods of modulating an immune response in an individual, which methods are also provided.

Immunomodulatory Peptides

The present disclosure provides immunomodulatory peptides. The peptides modulate an immune response to a virus in an individual.

In some cases, an immunomodulatory peptide of the present disclosure inhibits binding of an interferon-lambda (IFN-λ) polypeptide to an IL-28 receptor (IL-28R). For example, in some cases, an immunomodulatory peptide of the present disclosure inhibits binding of an IFN-λ polypeptide (e.g., a full-length, naturally-occurring IFN-λ polypeptide) to the IL-28R by at least about 10%, at least about 15%, at least about 20%, at least about 25%, at least about 30%, at least about 40%, at least about 50%, at least about 60%, at least about 70%, at least about 80%, at least about 90%, or more than 90%, compared to the binding of the IFN-λ polypeptide to the IL-28R in the absence of the immunomodulatory peptide. A peptide of the present disclosure that inhibits binding of an IFN-λ polypeptide to the IL-28R can be a peptide derived from an IFN-λ polypeptide, or can be a peptide derived from the IL-28R.

In some cases, an immunomodulatory peptide of the present disclosure inhibits viral replication in a virus-infected cell. For example, in some instances, an immunomodulatory peptide of the present disclosure, when contacted with a virus-infected cell, inhibits viral replication in the virus-infected cell by at least about 10%, at least about 15%, at least about 20%, at least about 25%, at least about 30%, at least about 40%, at least about 50%, at least about 60%, at least about 70%, at least about 80%, at least about 90%, or more than 90%, compared to the degree of viral replication in the virus-infected cell not contacted with the peptide.

In some cases, an immunomodulatory peptide of the present disclosure increases production of immunoglobulin in an individual. For example, in some instances, an immunomodulatory peptide of the present disclosure, when administered to an individual, increases production of immunoglobulin by at least about 10%, at least about 25%, at least about 50%, at least about 100% (or 2-fold), at least about 2.5-fold, at least about 5-fold, at least about 10-fold, or more than 10-fold, compared to the level of production of immunoglobulin in the individual not treated with the peptide.

In some cases, an immunomodulatory peptide of the present disclosure binds an IL-28R1 (IL-28R alpha subunit) polypeptide (e.g., human IL-28R1) with a $K_D$ of from about 0.01 nM to about 15 nM, e.g., from about 0.01 nM to about 0.05 nM, from about 0.05 nM to about 0.1 nM, from about 0.1 nM to about 0.5 nM, from about 0.5 nM to about 1.0 nM from about 1.0 nM to about 2 nM, from about 2 nM to about 5 nM, from about 5 nM to about 10 nM, or from about 10 nM to about 15 nM.

Peptides that Inhibit Binding to an IL-28R; Derived from an IFN-λ Polypeptide As noted above, an immunomodulatory peptide of the present disclosure includes a peptide that inhibits binding of an IFN-λ polypeptide to an IL-28R includes a peptide derived from an IFN-λ polypeptide.

A peptide that is derived from an IFN-λ polypeptide and that inhibits binding of an IFN-λ polypeptide to an IL-28R can have a length of up to 100 amino acids; for example, a peptide derived from an IFN-λ polypeptide can have a length of from about 8 amino acids (aa) to about 10 aa, from about 10 as to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to 80 aa, from about 80 aa to about 90 aa, or from about 90 aa to about 100 aa. In some cases, a peptide derived from an IFN-λ polypeptide has a length of 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa.

An immunomodulatory peptide that is derived from an IFN-λ polypeptide and that inhibits binding of an IFN-λ polypeptide to an IL-28R can comprise from about 8 contiguous amino acids to about 100 contiguous amino acids of an amino acid sequence having at least about 85%, at least about 90%, at least about 95%, at least about 98%, at least about 99%, or 100%, amino acid sequence identity to a human IL-29 polypeptide. For example, an immunomodulatory peptide that is derived from an IFN-λ polypeptide and that inhibits binding of an IFN-λ polypeptide to an IL-28R can comprise from about 8 contiguous amino acids to about 100 contiguous amino acids (e.g., 8, 9, 10, 11, 12, 13, 14, 15, 16, 17, 18, 19, 20, 21, 22, 23, 24, or 25 contiguous amino acids; or 25-30, 30-40, 40-50, 50-60, 60-70, 70-80, 80-90, or 90-100 contiguous amino acids) of an amino acid sequence having at least about 85%, at least about 90%, at least about 95%, at least about 98%, at least about 99%, or 100%, amino acid sequence identity to the IL-29 amino acid sequence depicted in FIG. 3.

An immunomodulatory peptide that is derived from an IFN-λ polypeptide and that inhibits binding of an IFN-λ polypeptide to an IL-28R can comprise from about 8 contiguous amino acids to about 100 contiguous amino acids of an amino acid sequence having at least about 85%, at least about 90%, at least about 95%, at least about 98%, at least about 99%, or 100%, amino acid sequence identity to a human IL-28A polypeptide. For example, an immunomodulatory peptide that is derived from an IFN-λ polypeptide and that inhibits binding of an IFN-λ polypeptide to an IL-28R can comprise from about 8 contiguous amino acids to about 100 contiguous amino acids (e.g., 8, 9, 10, 11, 12, 13, 14, 15, 16, 17, 18, 19, 20, 21, 22, 23, 24, or 25 contiguous amino acids; or 25-30, 30-40, 40-50, 50-60, 60-70, 70-80, 80-90, or 90-100 contiguous amino acids) of an amino acid sequence having at least about 85%, at least about 90%, at least about 95%, at least about 98%, at least about 99%, or 100%, amino acid sequence identity to the IL-28A amino acid sequence depicted in FIG. 4.

An immunomodulatory peptide that is derived from an IFN-λ polypeptide and that inhibits binding of an IFN-λ polypeptide to an IL-28R can comprise from about 8 contiguous amino acids to about 100 contiguous amino acids of an amino acid sequence having at least about 85%, at least about 90%, at least about 95%, at least about 98%, at least about 99%, or 100%, amino acid sequence identity to a human IL-28B polypeptide. For example, an immunomodulatory peptide that is derived from an IFN-λ polypeptide and that inhibits binding of an IFN-λ polypeptide to an IL-28R can comprise from about 8 contiguous amino acids to about 100 contiguous amino acids (e.g., 8, 9, 10, 11, 12, 13, 14, 15, 16, 17, 18, 19, 20, 21, 22, 23, 24, or 25 contiguous amino acids; or 25-30, 30-40, 40-50, 50-60, 60-70, 70-80, 80-90, or 90-100 contiguous amino acids) of an amino acid sequence having at least about 85%, at least about 90%, at least about 95%, at least about 98%, at least about 99%, or 100%, amino acid sequence identity to the IL-28B amino acid sequence depicted in FIG. 5.

An immunomodulatory peptide that is derived from an IFN-λ polypeptide and that inhibits binding of an IFN-λ polypeptide to an IL-28R can comprise from about 8 contiguous amino acids to about 100 contiguous amino acids of an amino acid sequence having at least about 85%, at least about 90%, at least about 95%, at least about 98%, at least about 99%, or 100%, amino acid sequence identity to a human IFN-λ4 polypeptide. For example, an immunomodulatory peptide that is derived from an IFN-λ4 polypeptide and that inhibits binding of an IFN-λ polypeptide to an IL-28R can comprise from about 8 contiguous amino acids to about 100 contiguous amino acids (e.g., 8, 9, 10, 11, 12, 13, 14, 15, 16, 17, 18, 19, 20, 21, 22, 23, 24, or 25 contiguous amino acids; or 25-30, 30-40, 40-50, 50-60, 60-70, 70-80, 80-90, or 90-100 contiguous amino acids) of an amino acid sequence having at least about 85%, at least about 90%, at least about 95%, at least about 98%, at least about 99%, or 100%, amino acid sequence identity to the IFN-λ4 amino acid sequence depicted in FIG. 13.

In an exemplary embodiment, an immunomodulatory peptide that is derived from an IFN-λ polypeptide and that inhibits binding of an IFN-λ polypeptide to an IL-28R comprises the amino acid sequence $ELX_1X_2FKX_3AX_4DALEESLX_5L$ (SEQ ID NO: 10), where $X_1$ is A or Q; $X_2$ is S or A; $X_3$ is K or R; $X_4$ is R or K; and $X_5$ is K or L.

For example, an immunomodulatory peptide that is derived from an IFN-λ polypeptide and that inhibits binding of an IFN-λ polypeptide to an IL-28R can comprise the amino acid sequence ELASFKKARDALEESLKL (SEQ ID NO: 11). ELASFKKARDALEESLKL (SEQ ID NO:11) is also referred to as "Pep1" (e.g., in FIG. 7).

As another example, an immunomodulatory peptide can comprise the amino acid sequence ELQAFKRAKDALEESLLL (SEQ ID NO:12). ELQAFKRAKDALEESLLL is also referred to as "Pep2" (e.g., in FIG. 7).

As another example, an immunomodulatory peptide can comprise the amino acid sequence ELQAFKKAKDAIEKRLLE (SEQ ID NO:69). As another example, an immunomodulatory peptide can comprise the amino acid sequence ELQAFKKAKGAIEKRLLE (SEQ ID NO:70).

In another exemplary embodiment, an immunomodulatory peptide comprises the amino acid sequence $ASVTFNLFRLLTRDLX_1X_2$ (SEQ ID NO:13), where $X_1$ is K or N; and $X_2$ is Y or C.

For example, an immunomodulatory peptide can comprise the amino acid sequence ASVTFNLFRLLTRDLKY (SEQ ID NO:15). As another example, an immunomodulatory peptide can comprise the amino acid sequence ASVTFNLFRLLTRDLNC (SEQ ID NO: 16).

In another exemplary embodiment, an immunomodulatory peptide comprises the amino acid sequence $X_1SVTX_2NLFX_3LLTRDLX_4X_5$ (SEQ ID NO:82) where $X_1$ is A or D; $X_2$ is S or F; $X_3$ is R or Q; $X_4$ is K or N; and $X_5$ is Y or C. For example, an immunomodulatory peptide can comprise the amino acid sequence DSVTSNLFRLLTRDLKC (SEQ ID NO:71). As another example, an immunomodulatory peptide can comprise the amino acid sequence DSVTSNLFQLLLRDLKC (SEQ ID NO:72). As another example, an immunomodulatory peptide can comprise the amino acid sequence ASVTFNLFRLLTRDLKY (SEQ ID NO: 15). As another example, an immunomodulatory peptide can comprise the amino acid sequence ASVTFNLFRLLTRDLNC (SEQ ID NO:16).

In another exemplary embodiment, an immunomodulatory peptide comprises the amino acid sequence $X_1$VLGLAVAG$X_2$ (SEQ ID NO:83), where each of $X_1$ and $X_2$, if present, is from 1 to 10 amino acids (e.g., 1 amino acid (aa), 2 aa, 3 aa, 4 aa, 5 aa, 6 aa, 7 aa, 8 aa, 9 aa, or 10 aa) in length. For example, $X_1$ can comprise the amino acid sequence TL, VLVTL (SEQ ID NO:84), or WTVVLVTL (SEQ ID NO:85); and $X_2$ can comprise the amino acid sequence PVP, PVPTS (SEQ ID NO:86), or PVPTSKPT (SEQ ID NO:87).

In another exemplary embodiment, an immunomodulatory peptide comprises the amino acid sequence $X_1$TSKPTTTGK$X_2$ (SEQ ID NO:88), where each of $X_1$ and $X_2$, if present, is from 1 to 10 amino acids (e.g., 1 amino acid (aa), 2 aa, 3 aa, 4 aa, 5 aa, 6 aa, 7 aa, 8 aa, 9 aa, or 10 aa) in length. For example, $X_1$ can comprise the amino acid sequence GLAVAGPVP (SEQ ID NO:89), AVAGPVP (SEQ ID NO:90), AGPVP (SEQ ID NO:91), or GPVP (SEQ ID NO:92); and $X_2$ can be G (glycine), or can comprise the amino acid sequence GCH or GCHIG (SEQ ID NO:93).

In another exemplary embodiment, an immunomodulatory peptide comprises the amino acid sequence $X_1$GCHIGRFK$X_2$ (SEQ ID NO:94), where each of $X_1$ and $X_2$, if present, is from 1 to 10 amino acids (e.g., 1 amino acid (aa), 2 aa, 3 aa, 4 aa, 5 aa, 6 aa, 7 aa, 8 aa, 9 aa, or 10 aa) in length. For example, $X_1$ can be K (lysine) or can comprise the amino acid sequence GK, TGK, TTTGK (SEQ ID NO:95), PTTTGK (SEQ ID NO:96), or SKPTTTGK (SEQ ID NO:97); and $X_2$ can comprise the amino acid sequence SLS, SLSP (SEQ ID NO:98), SLSPQ (SEQ ID NO:99), SLSPQE (SEQ ID NO:100), SLSPQEL (SEQ ID NO:101). SLSPQELA (SEQ ID NO: 102), or SLSPQELAS (SEQ ID NO: 103).

In another exemplary embodiment, an immunomodulatory peptide comprises the amino acid sequence $X_1$QPLHTLHHIL$X_2$ (SEQ ID NO:104), where each of $X_1$ and $X_2$, if present, is from 1 to 10 amino acids (e.g., 1 amino acid (aa), 2 aa, 3 aa, 4 aa, 5 aa, 6 aa, 7 aa, 8 aa, 9 aa, or 10 aa) in length. For example, $X_1$ can comprise the amino acid sequence LD, DVLD (SEQ ID NO:105), or LEDVLD (SEQ ID NO: 106); $X_2$ can comprise the amino acid sequence SQ, SQLQ (SEQ ID NO: 107), or SQLQAC (SEQ ID NO: 108).

As further exemplary embodiments, an immunomodulatory peptide comprises one of the following the amino acid sequences, where the peptides are derived from IL-29; WTVVLVTLVLGLAVAG (SEQ ID NO:44); VLVTLVLGLAVAGPVP (SEQ ID NO:45); TLVLGLAVAGPVPTS (SEQ ID NO:46); VLGLAVAGPVPTSKPT (SEQ ID NO:47); GLAVAGPVPTSKPTTTGK (SEQ ID NO:48); AVAGPVPTSKPTTTGK (SEQ ID NO:49); AGPVPTSKPTTTGKG (SEQ ID NO:50); GPVPTSKPTTTGKGCH (SEQ ID NO:51); TSKPTTTGKGCHIG (SEQ ID NO:52); SKPTTTGKGCHIGRFK (SEQ ID NO:53); PTTTGKGCHIGRFKSLS (SEQ ID NO:54); TTTGKGCHIGRFKSLSP (SEQ ID NO:55); TTGKGCHIGRFKSLSP (SEQ ID NO:56); TGKGCHIGRFKSLSPQ (SEQ ID NO:57); GKGCHIGRFKSLSPQE (SEQ ID NO:58); KGCHIGRFKSLSPQEL (SEQ ID NO:59); KGCHIGRFXLSPQELA (SEQ ID NO:60); GCHIGRFKSLSPQELAS (SEQ ID NO:61); CHIGRFKSLSPQELASF (SEQ ID NO:62); HIGRFKSLSPQELASFK (SEQ ID NO:63); IGRFKSLSPQELASFKK (SEQ ID NO:64); LEDVLDQPLHTLHHIL (SEQ ID NO:65); DVLDQPLHTLHHILSQ (SEQ ID NO:66); LDQPLHTLHHILSQLQ (SEQ ID NO:67); and QPLHTLHHILSQLQAC (SEQ ID NO:68).

Peptides that Inhibit Binding to an IL-28R; Derived from an IL-28R Polypeptide

As noted above, an immunomodulatory peptide of the present disclosure includes a peptide that inhibits binding of an IFN-λ polypeptide to an IL-28R includes a peptide derived from an IL-28R polypeptide. An immunomodulatory peptide derived from an IL-28R polypeptide can be derived from an IL-28R1 polypeptide or can be derived from an IL-10R2 polypeptide.

A peptide that is derived from an IL-28R polypeptide and that inhibits binding of an IFN-λ polypeptide to an IL-28R can have a length of up to 100 amino acids; for example, a peptide derived from an IL-28R polypeptide can have a length of from about 8 amino acids (aa) to about 10 aa, from about 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to 80 aa, from about 80 aa to about 90 aa, or from about 90 aa to about 100 aa. In some cases, a peptide derived from an IL-28R polypeptide has a length of 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa.

Immunomodulatory Peptides Derived from IL-28R1

An immunomodulatory peptide that is derived from an IL-28R polypeptide and that inhibits binding of an IFN-λ polypeptide to an IL-28R can comprise from about 8 contiguous amino acids to about 100 contiguous amino acids (e.g., 8, 9, 10, 11, 12, 13, 14, 15, 16, 17, 18, 19, 20, 21, 22, 23, 24, or 25 contiguous amino acids; or 25-30, 30-40, 40-50, 50-60, 60-70, 70-80, 80-90, or 90-100 contiguous amino acids) of an amino acid sequence having at least about 85%, at least about 90%, at least about 95%, at least about 98%, at least about 99%, or 100%, amino acid sequence identity to the IL-28R-α amino acid sequence depicted in FIG. 6. In some cases, the immunomodulatory peptide has a length of 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, the immunomodulatory peptide has a length of from about 25 aa to about 30 aa, from about 30 aa to about 40 aa, from about 40 aa to about 50 aa, from about 50 aa to about 60 aa, from about 60 aa to about 70 aa, from about 70 aa to 80 aa, from about 80 aa to about 90 aa, or from about 90 aa to about 100 aa.

For example, an immunomodulatory can comprise the amino acid sequence VAYQSSPTRRRWREV (SEQ ID NO:24); MMCLKKQDLYNKFKG (SEQ ID NO:25); SEYLDYLFEVEPAPP (SEQ ID NO:26); NATYQLPPCMPPLDLKY(SEQ ID NO:27); or ARTIYTFSVPKYSKF (SEQ ID NO:28); or an amino acid sequence having from 1 to 5 conservative amino acid substitutions compared to VAYQSSPTRRRWREV (SEQ ID NO:24), MMCLKKQDLYNKFKG (SEQ ID NO:25), SEYLDYLFEVEPAPP (SEQ ID NO:26), NATYQLPPCMPPLDLKY(SEQ ID NO:27), or ARTIYTFSVPKYSKF (SEQ ID NO:28).

Immunomodulatory Peptides Derived from IL-10R2

An immunomodulatory peptide that is derived from an IL-28R polypeptide and that inhibits binding of an IFN-λ polypeptide to an IL-28R can comprise from about 8 contiguous amino acids to about 100 contiguous amino acids (e.g., 8, 9, 10, 11, 12, 13, 14, 15, 16, 17, 18, 19, 20, 21, 22, 23, 24, or 25 contiguous amino acids; or 25-30, 30-40, 40-50, 50-60, 60-70, 70-80, 80-90, or 90-100 contiguous amino acids) of an amino acid sequence having at least about 85%, at least about 90%, at least about 95%, at least about 98%, at least about 99%, or 100%, amino acid sequence identity to the IL-10 receptor-2 (IL-10R2) amino acid sequence depicted in FIG. 18.

An immunomodulatory peptide can comprise an amino acid sequence derived from an IL-10R2 polypeptide. For example, an immunomodulatory peptide can comprise the amino acid sequence ECDFSSLSKYGDHTLRV (SEQ ID NO:36). As another example, an immunomodulatory peptide can comprise the amino acid sequence FTAQYLSYRIFQDKC (SEQ ID NO:37). As another example, an immunomodulatory peptide can comprise the amino acid sequence TAQYLSYRIFQDKCM (SEQ ID NO:38). As another example, an immunomodulatory peptide can comprise the amino acid sequence ECDFSSLSKYGDHTLR (SEQ ID NO:39). As another example, an immunomodulatory peptide can comprise the amino acid sequence GMQVEVLADCLHMRFLA (SEQ ID NO:40). As another example, an immunomodulatory peptide can comprise the amino acid sequence QVEVLADCLHMRFLAPKIENE (SEQ ID NO:41). As another example, an immunomodulatory peptide can comprise the amino acid sequence CLHMRFLAPKIENE (SEQ ID NO:42). As another example, an immunomodulatory peptide can comprise the amino acid sequence FLAPKIENEYETWTM (SEQ ID NO:43). An immunomodulatory peptide can comprise an amino acid sequence having from 1 to 5 conservative amino acid substitutions compared to ECDFSSLSKYGDHTLRV (SEQ ID NO:36), FTAQYLSYRIFQDKC (SEQ ID NO:37), TAQYLSYRIFQDKCM (SEQ ID NO:38), ECDFSSLSKYGDHTLR (SEQ ID NO:39), GMQVEVLADCLHMRFLA (SEQ ID NO:40), QVEVLADCLHMRFLAPKIENE (SEQ ID NO:41), CLHMRFLAPKIENE (SEQ ID NO:42), or FLAPKIENEYETWTM (SEQ ID NO:43).

Amide Bond Substitutions

In some cases, a subject immunomodulatory peptide includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of a subject immunomodulatory peptide can be substituted.

In another example, one or more amide linkages (—CO—NH—) in a subject immunomodulatory peptide can be replaced with a linkage which is an isostere of an amide linkage, such as $—CH_2NH—$, $CH_2S—$, $—CH_2CH_2—$, CH═CH-(cis and trans), $—COCH_2—$, $—CH(OH)CH_2—$ or $—CH_2SO—$. One or more amide linkages in a subject immunomodulatory peptide can also be replaced by, for example, a reduced isostere pseudopeptide bond. See Couder et al. (1993) Int. J. Peptide Protein Res. 41:181-184. Such replacements, and methods of making such replacements, are known to those of ordinary skill in the art.

In some cases, a subject immunomodulatory peptide includes one or more linkages other than peptide bonds, e.g., at least two adjacent amino acids are joined via a linkage other than an amide bond. For example, to reduce or eliminate undesired proteolysis or other degradation pathways and/or to increase serum stability and/or to restrict or increase conformational flexibility, one or more amide bonds within the backbone of a subject immunomodulatory peptide can be substituted.

For example, one or more amide linkages (—CO—NH—) in a subject immunomodulatory peptide can be replaced with another linkage which is an isostere such as: $—CH_2NH—$, $CH_2S—$, $—CH_2CH_2—$, —CH═CH-(cis and trans), $—COCH_2—$, $—CH(OH)CH_2—$ and $—CH_2SO—$. This replacement can be made by methods known in the art.

As another example, one or more amide linkages in a subject immunomodulatory peptide can be replaced with a reduced isostere pseudopeptide bond. Couder et al. (1993) *Int. J. Peptide Protein Res.* 41:181-184.

Amino Acid Substitutions

One or more amino acid substitutions can be made in a subject immunomodulatory peptide. A subject immunomodulatory peptide can comprise one, two, or three amino acid substitutions (e.g., conservative amino acid substitutions), relative to the amino acid sequence of any one of the above-described amino acid sequences.

The term "conservative amino acid substitution" generally refers to substitution of amino acid residues within the following groups:

1) L, I, M, V, F;
2) R, K;
3) F, Y, H, W, R;
4) G, A, T, S;
5) Q, N; and
6) D, E.

Conservative amino acid substitutions in the context of a subject peptide are selected so as to preserve activity of the peptide. Such presentation may be preserved by substituting with an amino acid with a side chain of similar acidity, basicity, charge, polarity, or size to the side chain of the amino acid being replaced. Guidance for substitutions, insertion, or deletion may be based on alignments of amino acid sequences of different variant proteins or proteins from different species. For example, at certain residue positions that are fully conserved, substitution, deletion or insertion may not be allowed while at other positions where one or more residues are not conserved, an amino acid change can be tolerated. Residues that are semi-conserved may tolerate changes that preserve charge, polarity, and/or size.

In some cases, a subject immunomodulatory peptide comprises one or more modifications. For example, a subject immunomodulatory peptide can be cyclized.

As another example, a subject immunomodulatory peptide can have one or more amino acid modifications. A subject immunomodulatory peptide can include one or more D-amino acids.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are peptides that have phosphorylated amino acid residues, e.g. phosphotyrosine, phosphoserine, or phosphothreonine. In some instances, a subject immunomodulatory peptide comprises one or more phosphorylated amino acids. In some instances, a subject immunomodulatory peptide comprises one or more phosphotyrosine residues.

Also provided in the subject disclosure are peptides that have been modified using ordinary molecular biological techniques and synthetic chemistry so as to improve their resistance to proteolytic degradation or to optimize solubility properties or to render them more suitable for use in a method involving administering the peptide to an individual. Analogs of such peptides include those containing residues other than naturally occurring L-amino acids, e.g., D-amino acids or non-naturally occurring synthetic amino acids (e.g., non-natural, non-encoded amino acids).

The following are non-limiting examples of amino acid modifications that can be made to a subject immunomodulatory peptide:

a) substitution of alkyl-substituted hydrophobic amino acids: including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids: including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains: including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residues: including asparagine, glutamine, and alkyl or aromatic substituted derivatives of asparagine or glutamine; and f) substitution of hydroxyl containing amino acids: including serine, threonine, homoserine, 2,3-diaminopropionic acid, and alkyl or aromatic substituted derivatives of serine or threonine.

In some cases, a subject immunomodulatory peptide comprises one or more naturally occurring non-genetically encoded L-amino acids, synthetic L-amino acids or D-enantiomers of an amino acid. A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof.

For example, a subject immunomodulatory peptide can comprise only D-amino acids. For example, a subject immunomodulatory peptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

An immunomodulatory peptide of the present disclosure may be joined to a wide variety of other peptides or proteins for a variety of purposes. By providing for expression of the subject peptides, various post-translational modifications may be achieved. For example, by employing the appropriate coding sequences, one may provide farnesylation or prenylation. In this situation, the peptide will be bound to a lipid group at a terminus, so as to be able to be bound to a lipid membrane, such as a liposome.

A cysteine residue or a cysteine analog can be introduced into a subject immunomodulatory peptide to provide for linkage to another peptide via a disulfide linkage or to provide for cyclization of a subject immunomodulatory peptide. Methods of introducing a cysteine or cysteine analog are known in the art: see, e.g., U.S. Pat. No. 8,067,532.

A subject immunomodulatory peptide can be cyclized. One or more cysteine or cysteine analogs can be introduced into a subject immunomodulatory peptide, where the introduced cysteine or cysteine analog can form a disulfide bond with a second introduced cysteine or cysteine analog. Other means of cyclization include introduction of an oxime linker or a lanthionine linker: see, e.g., U.S. Pat. No. 8,044,175. Any combination of amino acids (or non-amino acid moiety) that can form a cyclizing bond can be used and/or introduced. A cyclizing bond can be generated with any combination of amino acids (or with amino acid and —$(CH_2)_n$—CO— or —$(CH_2)_n$—$C_6H_4$—CO—) with functional groups which allow for the introduction of a bridge. Some examples are disulfides, disulfide mimetics such as the —$(CH_2)_n$—carba bridge, thioacetal, thioether bridges (cystathionine or lanthionine) and bridges containing esters and ethers.

As one non-limiting example, a cyclic peptide can comprise the amino acid sequence:
KGQCTFTAQYLCSYRICFQDKCMQTTLTE CDFSSLSKYGDHTLRVRAECA (SEQ ID NO: 109), where the Lys at the N-terminus is covalently linked to the Ala at the C terminus. One or more disulfide bonds can be present between the underlined Cys residues.

Other modifications include, for example, an N-alkyl (or aryl) substitution (ψ[CONR]), or backbone crosslinking to construct lactams and other cyclic structures. Other derivatives of a subject immunomodulatory peptide include C-terminal hydroxymethyl derivatives, O-modified derivatives (e.g., C-terminal hydroxymethyl benzyl ether), N-terminally modified derivatives including substituted amides such as alkylamides and hydrazides.

In some cases, one or more L-amino acids in a subject immunomodulatory peptide is replaced with a D-amino acid.

In some cases, a subject immunomodulatory peptide is a retroinverso analog. Sela and Zisman (1997) *FASEB J.* 11:449. Retro-inverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids. See, e.g. Jameson et al. (1994) *Nature* 368:744; and Brady et al. (1994) *Nature* 368:692.

The carboxyl group $COR_3$ of the amino acid at the C-terminal end of a subject immunomodulatory peptide can be present in a free form ($R_3$=OH) or in the form of a physiologically tolerated alkaline or alkaline earth salt such as e.g. a sodium, potassium or calcium salt. The carboxyl group can also be esterified with primary, secondary or tertiary alcohols such as e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched $C_1$-$C_6$-alkylamines or $C_1$-$C_6$ di-alkylamines, e.g., methylamine or dimethylamine.

The amino group of the amino acid $NR_1R_2$ at the N-terminus of a subject immunomodulatory peptide can be present in a free form ($R_1$=H and $R_2$=H) or in the form of a physiologically tolerated salt such as e.g., a chloride or acetate. The amino group can also be acetylated with acids so that $R_1$=H and $R_2$=acetyl, trifluoroacetyl, or adamantyl. The amino group can be present in a form protected by conventional amino protecting groups of peptide chemistry such as e.g., Fmoc, Z, Boc, or Alloc. The amino group can be N-alkylated in which $R_1$ and/or $R_2$=$C_1$-$C_6$ alkyl or $C_2$-$C_8$ alkenyl or $C_7$-$C_9$ aralkyl.

Alkyl residues can be straight-chained, branched or optionally cyclic alkyl residues, e.g., methyl, ethyl, isopropyl and cyclohexyl.

One way to modify a subject immunomodulatory peptide is to conjugate (e.g. link) one or more additional elements at the N- and/or C-terminus of the peptide, such as another protein (e.g. having an amino acid sequence heterologous to the subject peptide) and/or a carrier molecule. Thus, an exemplary protein can be provided as fusion proteins with a polypeptide(s) derived from a subject immunomodulatory peptide.

Modifications that can enhance serum half-life of a subject immunomodulatory peptide are of interest. A subject immunomodulatory peptide may be "PEGylated", as containing one or more poly(ethylene glycol) (PEG) moieties. Methods and reagents suitable for PEGylation of a peptide are well known in the art and may be found in U.S. Pat. No. 5,849,860, disclosure of which is incorporated herein by reference. PEG suitable for conjugation to a peptide is generally soluble in water at room temperature, and has the general formula R(O—$CH_2$—$CH_2$)$_n$O—R, where R is hydrogen or a protective group such as an alkyl or an alkanol group, and where n is an integer from 1 to 1000. Where R is a protective group, it generally has from 1 to 8 carbons.

The PEG conjugated to a subject immunomodulatory peptide can be linear. The PEG conjugated to a subject immunomodulatory peptide may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

An isolated peptide of the present disclosure can be linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject immunomodulatory peptide comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject immunomodulatory peptide is covalently linked to a PEG polymer. See, e.g., Albrecht et al. (2006) *J. Immunol. Methods* 310:100. Methods and reagents suitable for PEGylation of a peptide are well known in the art and may be found in, e.g. U.S. Pat. No. 5,849,860. PEG suitable for conjugation to a peptide is generally soluble in water at room temperature, and has the general formula R(O—$CH_2$—$CH_2$)$_n$O—R, where R is hydrogen or a protective group such as an alkyl or an alkanol group, and where n is an integer from 1 to 1000. Where R is a protective group, it generally has from 1 to 8 carbons.

The PEG conjugated to a subject immunomodulatory peptide can be linear. The PEG conjugated to a subject immunomodulatory peptide may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

Where a subject immunomodulatory peptide is to be incorporated into a liposome, carbohydrate, lipid moiety, including N-fatty acyl groups such as N-lauroyl. N-oleoyl, fatty amines such as dodecyl amine, oleoyl amine, and the like (e.g., see U.S. Pat. No. 6,638,513) may also be used to modify the subject peptide.

A subject immunomodulatory peptide can be conjugated to a branched structure, such as a MAP4 configuration, in which peptides are linked to a lattice matrix of lysines. In a MAP4 configuration, branched structures are produced by initiating peptide synthesis at both the N-terminal and side chain amines of lysine. Depending upon the number of times lysine is incorporated into the sequence and allowed to branch, the resulting structure will present multiple N-termini.

A subject imnununomodulatory peptide can be a "stapled" peptide. See, e.g., Walensky et al. (2004) *Science* 305:1466; A stapled peptide is generated using α,α-disubstituted nonnatural amino acids containing olefin-bearing tethers to generate an all-hydrocarbon "staple" by ruthenium-catalyzed olefin metathesis. See, e.g., Schafmeister et al. (2000) *J. Am. Chem. Soc.* 122:5891; and Blackwell and Grubbs (1994) *Angew. Chem. Int. Ed Engl.* 37:3281.

In some cases, a subject immunomodulatory peptide is a peptoid, i.e., a subject peptide is a poly(N-substituted glycine), in which the side chains are appended to the nitrogen atom of the peptide backbone, rather than to the α-carbons. See, e.g., WO 94/06451, WO 98/06437, and WO 99/08711; U.S. Pat. No. 5,877,278; and Simon et al. (1992) *Proc. Natl. Acad. Sci. USA* 89:9367. Synthesis of peptoids is described in, e.g., U.S. Pat. No. 5,877,278; and Zuckerman et al. (1992) *J. Am. Chem. Soc.* 114:10646.

In some cases, a subject immunomodulatory peptide is a peptide mimotope. See, e.g., Smith and Petrenko (1997) *Chemical Reviews* 97: 391-410; and Tong et al. (2002) *Science* 295: 321-4.

A subject imnununomodulatory peptide can be conjugated to various moieties. For example, in some cases, a subject immunomodulatory peptide is a fusion protein comprising the immunomodulatory peptide and a fusion partner, where suitable fusion partners include, e.g., an immunoglobulin Fc. Thus, the present disclosure provides immunomodulatory peptide-Fc fusion polypeptides. Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, the Fc domain comprises immunoglobulin domains Cγ2 and Cγ3 (CH2 and CH3) and the hinge between Cγ1 (CH1) and Cγ2 (CH2). An immunomodulatory peptide-Fc fusion polypeptide can exhibit increased circulation half-life, compared to the circulation (serum) half-life of an immunomodulatory peptide not conjugated to an immunoglobulin Fc.

A subject immunomodulatory peptide can be conjugated to a single domain antibody (also referred to as a "nanobody"), i.e., an antibody fragment consisting of a single monomeric variable antibody domain. See, e.g., Dumoulin et al. (2002) *Protein Sci.* 11:500; and Caussinus et al. (2011) *Nat. Struct. Molec. Bio.* 19:117.

Methods of Making an Immunomodulatory Peptide

A subject immunomodulatory peptide can be isolated and purified in accordance with conventional methods of recombinant synthesis, in which an expression vector comprising a nucleotide sequence encoding the immunomodulatory peptide is introduced into an appropriate host cell, generating a recombinant expression host cell, where the recombinant expression host cell synthesizes the encoded peptide. A lysate may be prepared of the expression host and the lysate purified using high performance liquid chromatography (HPLC), exclusion chromatography, gel electrophoresis, affinity chromatography, or other purification technique. In some cases, the compositions which are used will comprise at least 80% by weight of the desired product, at least about 85% by weight, at least about 95% by weight, or at least about 99.5% by weight, in relation to contaminants related to the method of preparation of the product and its purification. The percentages can be based upon total protein.

A subject peptide may be prepared by in vitro chemical synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like. For example, solid-phase peptide synthesis (SPPS) allows the incorporation of unnatural amino acids and/or peptide/protein backbone modification. Various forms of SPPS, such as Fmoc and Boc, are available for synthesizing a subject peptide. Details of the chemical synthesis are known in the art (e.g., Ganesan A. 2006 *Mini Rev. Med Chem.* 6:3-10 and Camarero J A et al. 2005 *Protein Pept Lett.* 12:723-8).

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Where a subject immunomodulatory peptide is produced using recombinant techniques, the immunomodulatory peptide may be produced as an intracellular protein or as an secreted protein, using any suitable construct and any suitable host cell, which can be a prokaryotic or eukaryotic cell, such as a bacterial (e.g., *Escherichia coli*) cell or a yeast host cell, respectively. Other examples of eukaryotic cells that may be used as host cells include insect cells, mammalian cells, filamentous fungi, and plant cells. Suitable yeast cells include, e.g., *Saccharomyces cerevisiae* and *Pichia* (e.g., *Pichia pastoris*).

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, MRC5 cells (ATCC No. CCL-171), and the like. Where mammalian host cells are used, such host cells may include human cells (e.g. HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells). Also suitable for use are HFF-1 cells (human fibroblast cells; ATCC SCRC-1041). Also suitable for use are clone Huh7.5 of the Huh7 cell line.

A variety of host-vector systems suitable for the expression of a peptide may be employed according to standard procedures known in the art. See, e.g., Sambrook et al., 1989 Current Protocols in Molecular Biology Cold Spring Harbor Press, New York; Ausubel et al. 1995 Current Protocols in Molecular Biology, Eds. Wiley and Sons; "Protein Expression: A Practical Approach" (1999) S. J. Higgins and B. D. James, eds., Oxford University Press; "Protein Expression in Mammalian Cells: Methods and Protocols (Methods in Molecular Biology)" (2012) James L. Hartley, ed., Humana Press; and "Production of Recombinant Proteins" (2005) Gerd Gellisen, ed., Wiley-VCH. Methods for introduction of nucleic acids into host cells include, for example, transformation, electroporation, conjugation, calcium phosphate methods and the like. The method for transfer can be selected so as to provide for stable expression of the introduced peptide-encoding nucleic acid. The peptide-encoding nucleic acid can be provided as an inheritable episomal element (e.g., a plasmid) or can be genomically-integrated. A variety of appropriate vectors for use in production of a peptide of interest are available commercially.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, HIV-based lentiviral vectors, murine leukemia virus (MVL)-based gamma retrovirus vectors, and the like), lentiviral-based vectors with the tet on/off system, P1-based artificial chromosomes, yeast plasmids, yeast artificial chromosomes, and any other vectors specific for specific hosts of interest (such as $E.\ coli$, mammalian cells, insect cells, or yeast cells).

A subject immunomodulatory peptide can be produced by introducing a recombinant expression vector comprising a nucleotide sequence encoding the immunomodulatory peptide into an appropriate host cell, where the host cell produces the encoded immunomodulatory peptide. In the expression vector, a polynucleotide comprising a nucleotide sequence(s) encoding a subject immunomodulatory peptide is linked to a regulatory sequence as appropriate to obtain the desired expression properties. These regulatory sequences can include promoters, enhancers, terminators, operators, repressors, and inducers. The promoters can be regulated or constitutive. Expression vectors generally have convenient restriction sites located near the promoter sequence to provide for the insertion of nucleic acid sequences encoding a protein of interest. A selectable marker operative in the expression host cell may be present.

Antibodies

The present disclosure provides antibodies, e.g., isolated antibodies, that specifically bind an IL28R and that inhibit binding of an IFN-λ (IL-29, IL-28A, or IL-28B) to the IL-28R. An antibody of the present disclosure is also referred to as an "anti-IL28R antibody."

In some cases, a peptide used as an antigen to generate anti-L28R1 antibodies has a length of from about 15 amino acids to about 50 amino acids (e.g., from about 15 aa to about 20 aa, from about 20 aa to about 25 aa, from about 25 aa to about 30 aa, from about 30 aa to about 40 aa, from about 40 aa to about 50 aa), and has at least about 80%, at least about 85%, at least about 90%, at least about 95%, at least about 98%, at least about 99%, or 100%, amino acid sequence identity with a contiguous stretch of from about 15 amino acids to about 50 amino acids (e.g., from about 15 aa to about 20 aa, from about 20 aa to about 25 aa, from about 25 aa to about 30 aa, from about 30 aa to about 40 aa, from about 40 aa to about 50 aa) of the amino acid sequence depicted in FIG. 6 (L28R-α subunit).

Exemplary peptides suitable for use as antigens to generate anti-IL28R1 antibodies include, e.g.:

```
                                          (SEQ ID NO: 5)
GPLLLCLLQAAPGRPRLAPPQNVTLLSQNFSVYLTWLP;

(SEQ ID NO: 6)
DVTYFVAYQSSPTRRRWREVEECAGTKELLCSMMCLKKQ;

(SEQ ID NO: 7)
VRTVSPSSKSPWVESEYLDYLFEVEPAPPVLVLTQ;

(SEQ ID NO: 8)
SANATYQLPPCMPPLDLKYEVAFW;
and
                                          (SEQ ID NO: 9)
LFPVTPHGQPVQITLQPAASEHHCLSARTIYTFSVPKYSKF.
```

An antibody specific for an epitope on an IL-28R generally has an affinity of at least about $10^{-7}$ M, at least about $5 \times 10^{-7}$ M, at least about $10^{-8}$ M, at least about $5 \times 10^{-8}$ M, or at least about $10^{-9}$ M.

The term "antibody" (also used interchangeably with "immunoglobulin") encompasses polyclonal and monoclonal antibody preparations where the antibody may be of any class of interest (e.g., IgM, IgG, IgA, IgE, and subclasses thereof), as well as preparations including hybrid antibodies, altered antibodies, F(ab')$_2$ fragments, F(ab) molecules, Fv fragments, scFv fragments, single chain antibodies, single domain antibodies, chimeric antibodies, humanized antibodies, bivalent antibodies, bispecific antibodies, and functional fragments thereof which exhibit immunological binding properties of the parent antibody molecule. The antibodies may be conjugated to other moieties, and/or may be bound to a support (e.g., a solid support), such as a polystyrene plate, a bead, a test strip, and the like.

An "epitope" is a site on an antigen (e.g. an IL28R peptide) to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a spatial conformation. Methods of determining spatial conformation of epitopes include, for example, x-ray crystallography and 2-dimensional nuclear magnetic resonance. See, e.g.

Epitope Mapping Protocols in Methods in Molecular Biology, Vol. 66, Glenn E. Morris, Ed (1996).

Immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" comprise a variable region at the $NH_2$-terminus and a kappa or lambda constant region at the COOH-terminus. Full-length immunoglobulin "heavy chains" similarly comprise a variable region and one of the aforementioned heavy chain constant regions, e.g., gamma.

An immunoglobulin light or heavy chain variable region is composed of a "framework" region (FR) interrupted by three hypervariable regions, also called "complementarity determining regions" or "CDRs". CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996). Methods to define CDRs are available in the art and routinely performed. For example, framework regions and CDRs may be defined by IMGT (see, "Sequences of Proteins of Immunological Interest," E. Kabat et al., U.S. Department of Health and Human Services, (1991 and Lefranc et al. IMGT, the international ImMunoGeneTics information System®. Nucl. Acids Res., 2005, 33, D593-D597)). A detailed discussion of the IMGTS system, including how the IMGTS system was formulated and how it compares to other systems, is provided on the World Wide Web at imgt.cines.fr/textes/IMGTScientificChart/Numbering/IMGTnumberingsTable.html. The framework region of an antibody, that is the combined framework regions of the constituent light and heavy chains, serves to position and align the CDRs. The CDRs are primarily responsible for binding to an epitope of an antigen.

The term "monoclonal antibody" refers to an antibody composition having a homogeneous antibody population. The term is not limited by the manner in which it is made. The term encompasses whole immunoglobulin molecules, as well as Fab molecules, F(ab')2 fragments, Fv fragments, scFv, fusion proteins comprising an antigen-binding portion of an antibody and a non-antibody protein, and other molecules that exhibit immunological binding properties of the parent monoclonal antibody molecule. Methods of making polyclonal and monoclonal antibodies are known in the art.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$—$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example EP 404,097; WO 93/11161; and Hollinger et al., Proc. Natl. Acad. Sci. USA. 90:6444-6448 (1993).

A subject anti-IL28R antibody may be recombinant. The antibody may contain a light and/or heavy chain. Methods for producing recombinant antibodies are known in the art. For example, the nucleic acids encoding the antibody, or at least a complementary determining region (CDR) of a heavy chain polypeptide or at least a CDR of a light chain polypeptide, are introduced directly into a host cell, and the cell incubated under conditions sufficient to induce expression of the encoded antibody. The recombinant antibody may be glycosylated by an endogenous glycosylase in the host cells; the recombinant antibody may be unglycosylated; or the recombinant antibody may have an altered glycosylation pattern.

Where the antibody is recombinant, the antibody may be chimeric. Chimeric antibodies are immunoglobulin molecules comprising human and non-human portions. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody can have the antigen binding specificity of the non-human antibody molecule and the effector function conferred by the human antibody molecule. A large number of methods of generating chimeric antibodies are well known to those of skill in the art. An alternative approach is the generation of humanized antibodies by linking the CDR regions of non-human antibodies to human constant regions by recombinant DNA techniques.

A recombinant fusion antibody that is specific for an IL28R epitope is contemplated, in which the antibody is modified to include a heterologous protein. For example, a heavy chain polypeptide and/or light chain polypeptide may be joined to a reporter protein or to a protein having a desired therapeutic effect. The reporter protein may be a fluorescent protein. The antibody may also be conjugated to a second antibody (or at least an antigen-binding portion thereof). Methods for producing a fusion protein of interest when provided a nucleic acid sequence are well known in the art.

Humanized and Human Antibodies

A subject anti-IL28R antibody will in some embodiments be humanized. Amino acids may be substituted in the framework regions of a parent non-human (e.g., mouse monoclonal) antibody to produce a modified antibody that is less immunogenic in a human than the parent non-human antibody. Antibodies can be humanized using a variety of techniques known in the art. Framework substitutions are identified by modeling of the interactions of the CDR and framework residues to identify framework residues important for antigen binding and sequence comparison to identify unusual framework residues at particular positions.

The antibody may also be a fully human antibody. Human antibodies are primarily composed of characteristically human polypeptide sequences. A subject human antibody can be produced by a wide variety of methods. For example, human antibodies can be produced initially in trioma cells (descended from three cells, two human and one mouse). Genes encoding the antibodies are then cloned and expressed in other cells, particularly non-human mammalian cells. The general approach for producing human antibodies by trioma technology has been described in the art.

Accordingly, the present disclosure contemplates a DNA molecule comprising a nucleic acid sequence encoding an antibody that binds to an IL28R. The disclosure further contemplates recombinant host cells containing an exogenous polynucleotide encoding at least a CDR of a heavy chain polypeptide or at least a CDR of a light chain polypeptide of the subject antibody, scFv In some embodiments, a subject antibody comprises anti-IL28R antibody heavy chain CDRs and anti-IL28R antibody light chain CDRs in a single polypeptide chain, e.g., in some embodiments, a subject antibody is a scFv. In some embodiments, a subject antibody comprises, in order from N-terminus to C-terminus: a first amino acid sequence of from about 5 amino acids to about 25 amino acids in length; a heavy chain CDR1 of an anti-IL28R antibody; a second amino acid sequence of from about 5 amino acids to about 25 amino acids in length; a heavy chain CDR2 of an anti-IL28R antibody; a third amino acid sequence of from about 5 amino acids to about 25 amino acids in length; a heavy chain CDR3 of an anti-IL28R antibody; a fourth amino acid sequence of from about 5 amino acids to about 25 amino acids in length; a light chain CDR1 of an anti-IL28R antibody; a fifth amino acid sequence of from about 5 amino acids to about 25 amino acids in length; a light chain CDR2 an anti-IL28R antibody; a sixth amino acid sequence of from about 5 amino acids to about 25 amino acids in length; a light chain CDR3 an anti-IL28R antibody; and a seventh amino acid sequence of from about 5 amino acids to about 25 amino acids in length.

In some embodiments, a subject anti-IL28R antibody comprises scFv multimers. For example, in some embodiments, a subject anti-IL28R antibody is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFV multimer is humanized, as described above.

Immunomodulatory Peptide Compositions

The present disclosure provides compositions comprising a subject immunomodulatory peptide.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g. Remington's Pharmaceutical Sciences, Mack Publishing Company, Easton, Pa., 17th edition, 1985. The composition or formulation to be administered will, in any event, contain a quantity of a subject peptide adequate to achieve the desired state in the subject being treated.

A subject peptide can be formulated into a composition by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, lotions, and aerosols. As such, administration of a subject peptide can be achieved in various ways, including oral, vaginal, buccal, rectal, parenteral, intraperitoneal, intradermal, transdermal, intratracheal, etc., administration. A subject peptide can be systemic after administration or may be localized by the use of an implant or other formulation that acts to retain an active dose of the peptide at or near the site of administration.

For oral preparations, a subject peptide can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An immunomodulatory peptide of the present disclosure can be formulated into preparations for injections by dissolving, suspending or emulsifying the peptide in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Unit dosage forms for oral administration, such as syrups, elixirs, and suspensions, may be provided wherein each dosage unit, for example, teaspoonful, tablespoonful, tablet or suppository, contains a predetermined amount of one or more of a subject peptide. Similarly, unit dosage forms for injection or intravenous administration may comprise a peptide(s) of the present disclosure in a composition as a solution in sterile water, normal saline or another pharmaceutically acceptable carrier.

Implants for sustained release formulations are well-known in the art. Implants are formulated as microspheres, slabs, etc, with biodegradable or non-biodegradable polymers. For example, polymers of lactic acid and/or glycolic acid form an erodible polymer that is well tolerated by the host. An implant containing a subject peptide can be placed in proximity to a desired treatment site, so that the local concentration of active agent is increased at the treatment site relative to the rest of the body.

In some embodiments, a subject peptide is formulated in a controlled release formulation. Sustained-release preparations may be prepared using methods well known in the art. Suitable examples of sustained-release preparations include semipermeable matrices of solid hydrophobic polymers containing the peptide in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity of a peptide present in sustained-release preparations may be prevented or reduced by using appropriate additives, by controlling moisture content and by use of specific polymer matrix compositions.

A subject immunomodulatory peptide can be formulated in a liposome. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al (1991) J. Biol. Chem. 266:3361 may be used. Briefly, lipids and composition containing a subject peptide are combined in an appropriate aqueous medium, conveniently a saline medium where the total solids will be in the range of about 1-10 weight percent. After intense agitation for short periods of time, from about 5-60 seconds, the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Additional Adjuvants

In some embodiments, a composition comprising an isolated immunomodulatory peptide of the present disclosure also comprises an additional adjuvant, i.e., at least a second adjuvant. In some cases, a subject immunostimulatory peptide and a second adjuvant have a synergistic effect on an immune response.

Examples of known suitable adjuvants that can be used in humans include, but are not necessarily limited to, alum, aluminum phosphate, aluminum hydroxide, MF59 (4.3% w/v squalene, 0.5% w/v Tween 80™, 0.5% w/v Span 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants include, but are not limited to: (1) oil-in-water emulsion formulations (with or without other specific immunostimulating agents such as muramyl peptides (see below) or bacterial cell wall components), such as for example (a) MF59™ (see, e.g., WO 90/14837), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-9, IL-12, IL-13, etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions (see, e.g. EP-A-0835318, EP-A-0735898, EP-A-0761231); (7) oligonucleotides comprising a CpG motif containing at least one CG dinucleotide, where the cytosine is unmethylated (see, e.g., WO 96/02555, WO 98/16247, WO 98/18810, WO 98/40100, WO 98/55495, WO 98/37919 and WO 98/52581); (8) a polyoxyethylene ether or a polyoxyethylene ester (see, e.g. WO 99/52549); (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt (see, e.g. WO 00/23105); (12) a saponin and an oil-in-water emulsion (see e.g. WO 99/11241); (13) a saponin (e.g. QS21)+3dMPL+IM2 (optionally including a sterol) (see, e.g. WO 98/57659); (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Toll-like receptor (TLR) agonists (e.g., CpG oligonucleotides) are suitable for use. Also suitable for use is Matrix-M™; Matrix-M™ is an adjuvant that comprises 40 nm nanoparticles comprising *Quillaja* saponins, cholesterol, and phospholipid. Adjuvants suitable for administration to a human are of particular interest.

In some instances, the adjuvant is MF59, with or without a CpG-containing oligonucleotide. In other instances, the adjuvant is alum, with or without a CpG-containing oligonucleotide. In other instances, the adjuvant is poly(D,L- lactide-co-glycolide), with or without a CpG-containing oligonucleotide. In other instances, the adjuvant is MPL, with or without a CpG-containing oligonucleotide. In other cases, the adjuvant is Matrix-M™, with or without a CpG-containing oligonucleotide. In some embodiments, the additional adjuvant is MF59, alum, poly(DL-lactide co-glycolide), or a CpG oligonucleotide.

Peptide Mixtures

A composition comprising an isolated immunomodulatory peptide of the present disclosure can comprise two or more different immunomodulatory peptides. For instance, a composition comprising an isolated immunomodulatory peptide of the present disclosure can comprise 2, 3, 4, 5, or more different immunomodulatory peptides.

In some cases, a subject composition comprises:
a) a first subject immunomodulatory peptide, where the peptide is derived from an IFN-λ polypeptide, and where the peptide inhibits binding of an IFN-λ polypeptide to an IL-28R; and
b) at least a second subject immunomodulatory peptide, where the peptide is derived from an IFN-λ polypeptide, and where the peptide inhibits binding of an IFN-λ polypeptide to an IL-28R.

In other cases, a subject composition comprises:
a) a subject immunomodulatory peptide, where the peptide is derived from an IFN-λ polypeptide, and wherein the peptide inhibits binding of an IFN-λ polypeptide to an IL-28R; and
b) a subject immunomodulatory peptide, where the peptide is derived from an IL-28R, and wherein the peptide inhibits binding of an IFN-λ polypeptide to an IL-28R.

In some cases, a subject composition comprises:
a) a subject immunomodulatory peptide, where the peptide is derived from an IFN-λ polypeptide, and wherein the peptide inhibits binding of an IFN-λ polypeptide to an IL-28R; and
b) a subject immunomodulatory peptide, where the peptide is derived from an IL-28R1 polypeptide, and wherein the peptide inhibits binding of an IFN-λ polypeptide to an IL-28R.

In some cases, a subject composition comprises:
a) a subject immunomodulatory peptide, where the peptide is derived from an IFN-λ polypeptide, and wherein the peptide inhibits binding of an IFN-λ polypeptide to an IL-28R; and
b) a subject immunomodulatory peptide, where the peptide is derived from an IL-10R2 polypeptide, and wherein the peptide inhibits binding of an IFN-λ polypeptide to an IL-28R.

Compositions Comprising a Pathogen or a Pathogen Component

A composition comprising an immunomodulatory peptide of the present disclosure can further include a pathogen, or a component of a pathogen. Pathogens include, e.g., bacterial pathogens; viral pathogens; fungal pathogens (e.g., *Candida*); pathogenic protozoa (e.g. *Giardia* (*Giardia lamblia*), malarial parasites (e.g., *Plasmodium falciparum*), and toxoplasmosis-causing protozoa (e.g. *Toxoplasma gondii*); and helminths. Components of a pathogen can be polypeptide components. Where the pathogen component is a polypeptide, a subject composition can include the polypeptide per se, or a nucleic acid comprising a nucleotide sequence encoding the polypeptide.

In some cases, the pathogen is a virus, or a viral component. Thus, the present disclosure provides a composition comprising an immunomodulatory peptide of the present disclosure; and a virus or a component of a virus. For example, where an immune response to a particular virus is desired, the virus, or components of the virus, can be included in a subject immunomodulatory peptide composition.

Where the composition comprises a virus, the virus can be an inactivated virus (e.g., a non-replicating virus); a split-virus (e.g., a split-virus inactivated virus); or a live, attenuated virus.

In some embodiments, the virus a member of Orthomyxoviridae, e.g., an influenza virus. The virus can be any of the three types of influenza viruses: A, B, and C (influenza A subtype, an influenza B virus subtype, or an influenza C virus). The influenza virus can be any of a variety of subtypes of influenza A virus, e.g., any subtype of influenza A H5, influenza A H7, and influenza A H9. The influenza virus can be a virus of any of a variety of combinations of hemagglutinin (HA) and neuraminidase (NA) variants. Subtypes of influenza A virus include H1N1, H1N2, H3N2, and H5N1 subtypes. Avian influenza A virus includes avian influenza A virus of any one of the subtypes H5 and H7, including H5N1, H7N7, H9N2, H7N2, and H7N3 viruses.

In some cases, the virus is a DNA virus, e.g., an adenovirus, a polyomavirus, and the like.

In some cases, the virus is a member of Herpesviridae, e.g., cytomegalovirus, Epstein-Barr virus, and the like.

Where the composition comprises a viral component, the viral component can be a virus subunit, or a nucleic acid comprising a nucleotide sequence encoding the viral subunit. For example, where the viral component is a component of an influenza virus, the viral component can be an influenza virus-encoded protein, such as hemagglutinin or neuraminidase; or a nucleic acid comprising a nucleotide sequence encoding hemagglutinin or neuraminidase. As another example, where the viral component is a component of cytomegalovirus (CMV), the viral component can be a CMV envelope glycoprotein B; or a nucleic acid comprising a nucleotide sequence encoding CMV envelope glycoprotein B. The viral component can be any CMV-encoded viral component (e.g., any component encoded by the CMV genome), or a nucleic acid comprising a nucleotide sequence encoding the CMV viral component.

In Vitro and Ex Vivo Methods

The present disclosure provides methods of modulating a cellular response in vitro or ex vivo, the methods generally involving contacting a cell or a cell population in vitro or ex vivo with a subject immunomodulatory peptide, where the immunomodulatory peptide modulates a response by the cell or cell population. Cellular responses include, but are not limited to, proliferation; cytokine production and secretion; immunoglobulin production; and the like. In some cases, a cell is contacted with a subject immunomodulatory peptide in vitro. In some cases, a cell is contacted with a subject immunomodulatory peptide ex vivo.

Suitable cells include, e.g., B cells, T cells, T cell subsets (e.g., T regulatory cells; Th17 T cells; T follicular helper cells; cytotoxic T cells; helper T cells; Th9 cells; and the like). Suitable cells also include monocytes, macrophages, and dendritic cells. In some cases, a cell population is contacted with a subject immunomodulatory peptide. A cell population contacted with a subject immunomodulatory peptide can be substantially homogeneous, or can be heterogeneous.

For example, in some cases, contacting a cell or cell population with a subject immunomodulatory peptide in vitro or ex vivo induces proliferation of the cell or cell population, and provides for an increase in the number of cells of from about 0.5-fold to about $10^3$-fold, or more than $10^3$-fold.

As another example, in some cases, contacting a cell or cell population with a subject immunomodulatory peptide in vitro or ex vivo increases production of a cytokine by the cell or cell population by at least about 10%, at least about 25%, at least about 50%, at least about 100% (or 2-fold), at least about 2.5-fold, at least about 5-fold, at least about 10-fold, or more than 10-fold, compared to the amount of cytokine produced by the cell or cell population in the absence of the immunomodulatory peptide.

As another example, in some cases, e.g., where the cell population comprises B cells, contacting the cell population with a subject immunomodulatory peptide in vitro or ex vivo increases production of an immunoglobulin by a B cell present in the cell population by at least about 10%, at least about 25%, at least about 50%, at least about 100% (or 2-fold), at least about 2.5-fold, at least about 5-fold, at least about 10-fold, or more than 10-fold, compared to the amount of immunoglobulin produced by a B cell present in cell population in the absence of the immunomodulatory peptide. For example, where the cell population comprises B cells, and one or more of dendritic cells, monocytes, and macrophages, contacting the cell population with a subject immunomodulatory peptide in vitro or ex vivo increases production of an immunoglobulin by a B cell present in the cell population by at least about 10%, at least about 25%, at least about 50%, at least about 100% (or 2-fold), at least about 2.5-fold, at least about 5-fold, at least about 10-fold, or more than 10-fold, compared to the amount of immunoglobulin produced by the B cell present in cell population in the absence of the immunomodulatory peptide.

Where a cell is contacted with a subject immunomodulatory peptide ex vivo, the cell can be a T cell, a B cell, or a mixed population comprising B and T cells. In these embodiments, a cell population, which may be a mixed cell population or a substantially homogeneous cell population, obtained from an individual is contacted with subject immunomodulatory peptide ex vivo, to generate a modulated or expanded cell population; and the modulated or expanded cell population is introduced into a recipient individual. The recipient individual can be the same individual from whom the cell population was obtained. The recipient individual can be a different individual from the individual from whom the cell population was obtained.

Treatment Methods

The present disclosure provides methods of modulating an immune response in an individual, the methods generally involving administering to the individual an effective amount of an agent that blocks (e.g., inhibits) binding of an IFN-λ polypeptide (IL-28A, IL-28B, IL29, IFN-λ4) to an IL-28R. In some cases, the agent is a peptide that inhibits binding of an IFN-λ polypeptide to an IL-28R. In some cases, the agent is an immunomodulatory peptide of the present disclosure. In other cases, the agent is an anti-IL28R antibody.

Immunomodulatory Peptides

An immunomodulatory peptide of the present disclosure, or a composition comprising the peptide or mixture of peptides, when administered in one or more doses to an individual, can modulate an immune response in the individual. Thus, the present disclosure provides methods of modulating an immune response in an individual, the methods generally involving administering to an individual in need thereof an effective amount of immunomodulatory peptide of the present disclosure, or an effective amount of a composition comprising the peptide or mixture of peptides. For simplicity, where the discussion below refers to an "effective amount" of an immunomodulatory peptide, the amounts apply equally to a composition comprising the peptide or mixture of peptides.

In some cases, an "effective amount" of an immunomodulatory peptide of the present disclosure is an amount that, when administered to an individual in need thereof in one or more doses, increases an immune response in the individual. For example, an "effective amount" of an immunomodulatory peptide of the present disclosure can be an amount that, when administered to an individual in need thereof in one or more doses, increases an immune response in the individual by at least about 10%, at least about 25%, at least about 50%, at least about 100% (or 2-fold), at least about 2.5-fold, at least about 5-fold, at least about 10-fold, or more than 10-fold, compared to the level of the immune response in the absence of administration with the immunomodulatory peptide. An immune response can include one or more of: 1) increased B cell proliferation; 2) increased numbers of memory B cells; 4) increased numbers of helper T lymphocytes; 5) increased numbers of memory T cells; 6) increased antibody production; 3) increased numbers of cytotoxic T lymphocytes; 7) increased numbers of dendritic cells, or modulation of dendritic cell function; 8) increased numbers of Th9 cells; 9) increased numbers of any T cell subset (e.g., Th17 T cells; T follicular helper cells; etc.); 10) decreased numbers of Tregs (T regulatory cells); 11) a change in the activation state of dendritic cells; 12) a change in the activation state of macrophages; and 13) a change in the activation state of monocytes. A change in the activation state of a dendritic cell, a macrophage, or a monocyte can include, e.g., a change in cell surface receptor expression and/or a change in the cytokine(s) produced by the cell.

In some cases, an "effective amount" of an immunomodulatory peptide of the present disclosure is an amount that, when administered to an individual in need thereof in one or more doses, increases a Th2 response in the individual. For example, an "effective amount" of an immunomodulatory peptide of the present disclosure can be an amount that, when administered to an individual in need thereof in one or more doses, increases a Th2 response in the individual by at least about 10%, at least about 25%, at least about 50%, at least about 100% (or 2-fold), at least about 2.5-fold, at least about 5-fold, at least about 10-fold, or more than 10-fold, compared to the level of the Th2 response in the absence of administration with the immunomodulatory peptide.

In some cases, an "effective amount" of an immunomodulatory peptide of the present disclosure is an amount that, when administered to an individual in need thereof in one or more doses, increases the level of a factor (e.g., where the factor is one or more of IL4, IL5, IL9, IL13, IP10, CD40L, fractalkine, GRO, and sIL2R-α) in the individual by at least about 10%, at least about 25%, at least about 50%, at least about 100% (or 2-fold), at least about 2.5-fold, at least about 5-fold, at least about 10-fold, or more than 10-fold, compared to the level of the factor in the individual in the absence of administration with the immunomodulatory peptide.

In some cases, an "effective amount" of an immunomodulatory peptide of the present disclosure is an amount that, when administered to an individual in need thereof in one or more doses, increases the level of IL4, IL5, IL9, and IL13 in the individual by at least about 10%, at least about 25%, at least about 50%, at least about 100% (or 2-fold), at least about 2.5-fold, at least about 5-fold, at least about 10-fold, or more than 10-fold, compared to the level of IL4, IL5, IL9, and IL13 in the individual in the absence of administration with the immunomodulatory peptide.

In some cases, an "effective amount" of an immunomodulatory peptide of the present disclosure is an amount that, when administered to an individual in need thereof in one or more doses, decreases the level of IL1b and/or IL6 in the individual by at least about 10%, at least about 25%, at least about 50%, at least about 75%, or more than 75%, compared to the level of IL1b and/or IL6 in the individual in the absence of administration with the immunomodulatory peptide.

In some cases, an "effective amount" of an immunomodulatory peptide of the present disclosure is an amount that, when administered to an individual in need thereof in one or more doses, increases the level of IFN-α in the individual. For example, an "effective amount" of an immunomodulatory peptide of the present disclosure can be an amount that, when administered to an individual in need thereof in one or more doses, increases the IFN-α level in the individual by at least about 10%, at least about 25%, at least about 50%, at least about 100% (or 2-fold), at least about 2.5-fold, at least about 5-fold, at least about 10-fold, or more than 10-fold, compared to the level of IFN-α in the absence of administration with the immunomodulatory peptide.

In some cases, an "effective amount" of an immunomodulatory peptide of the present disclosure is an amount that, when administered to an individual in need thereof in one or more doses, increases the level of an anti-inflammatory interferon-stimulated gene (ISG) product in the individual by at least about 10%, at least about 25%, at least about 50%, at least about 100% (or 2-fold), at least about 2.5-fold, at least about 5-fold, at least about 10-fold, or more than 10-fold, compared to the level of the ISG product in the absence of administration with the immunomodulatory peptide. Anti-inflammatory ISG products include, e.g., SOCS1 and Usp18. A "gene product" can be an mRNA and/or a polypeptide.

In some cases, an "effective amount" of an immunomodulatory peptide of the present disclosure is an amount that, when administered to an individual in need thereof in one or more doses, reduces the level of a pro-inflammatory ISG product in the individual by at least about 10%, at least about 25%, at least about 50%, at least about 75%, or more than 75%, compared to the pro-inflammatory ISG product in the absence of administration with the immunomodulatory peptide. Pro-inflammatory ISG products include, e.g., MX1, OAS1, IFIT2, ISG15, and the like. A "gene product" can be an mRNA and/or a polypeptide.

In some cases, an "effective amount" of an immunomodulatory peptide of the present disclosure is an amount that, when administered to an individual in need thereof in one or more doses, increases the amount of virus-neutralizing antibody in the individual. For example, an "effective amount" of an immunomodulatory peptide of the present disclosure can be an amount that, when administered to an individual in need thereof in one or more doses, increases the level of neutralizing antibody to a virus individual by at least about 10%, at least about 25%, at least about 50%, at least about 100% (or 2-fold), at least about 2.5-fold, at least about 5-fold, at least about 10-fold, or more than 10-fold, compared to the level of neutralizing antibody in the absence of administration with the immunomodulatory peptide.

In some cases, an "effective amount" of an immunomodulatory peptide of the present disclosure is an amount that, when administered to an individual in need thereof in one or more doses, reduces replication of a virus in the individual. For example, an "effective amount" of an immunomodulatory peptide of the present disclosure can be an amount that, when administered to an individual in need thereof in one or more doses, reduces replication of a virus in the individual by at least about 10%, at least about 15%, at least about 20%, at least about 25%, at least about 30%, at least about 40%, at least about 50%, or more than 50%, compared to the level of viral replication in the absence of administration with the immunomodulatory peptide.

In some cases, an "effective amount" of an immunomodulatory peptide of the present disclosure is an amount that, when administered to an individual in need thereof in one or more doses, is effective to reduce one or more symptoms of asthma in the individual by at least about 10%, at least about 15%, at least about 20%, at least about 25%, at least about 30%, at least about 40%, at least about 50%, or more than 50%, compared to the severity of the symptom in the absence of administration with the immunomodulatory peptide.

Compositions comprising a subject immunomodulatory peptide that are suitable for use in a method of modulating an immune response are described above.

Conventional and pharmaceutically acceptable routes of administration include inhalational (e.g., intranasal), intramuscular, intratracheal, intrathecal, intraperitoneal, subcutaneous, intradermal, transdermal, topical (e.g. to the skin, to the eye, etc.), intravenous, rectal, oral, vaginal, ocular, intraocular, and other enteral and parenteral routes of administration. Routes of administration may be combined, if desired, or adjusted depending upon the peptide and/or the desired effect. A peptide can be administered in a single dose or in multiple doses. In some cases, the route of administration is oral. In some cases, the route of administration is intranasal (e.g., via inhalation). In some cases, the route of administration is subcutaneous (e.g., via injection). In some cases, the route of administration is intradermal (e.g., via injection). In some cases, the route of administration is intramuscular (e.g., via injection).

In some instances, the route of administration and/or mode of administration provides for systemic administration of a peptide of the present disclosure. In other instances, the route of administration and/or mode of administration provides for localized administration of a peptide of the present disclosure. Exemplary routes of administration include oral, intramuscular, subcutaneous, transdermal, intradermal, intranasal, and intravenous routes of administration. As noted above, administration can be by injection, or by implantation of a composition that provides for release of a peptide.

Although the dosage used will vary depending on the clinical goals to be achieved, a suitable dosage range of a subject immunomodulatory peptide includes, e.g., from about 1 ng to about 5 mg per unit dose, e.g., from about 1 ng to about 10 ng, from about 10 ng to about 25 ng, from about 25 ng to about 50 ng, from about 50 ng to about 100 ng, from about 100 ng to about 500 ng, from about 500 ng to about 1 µg, from about 1 µg to about 5 µg, from about 5 µg to about 10 µg, from about 10 µg to about 25 µg, from about 25 µg to about 50 µg, from about 50 µg to about 100 µg, from about 100 µg to about 150 µg, from about 150 µg to about 250 µg, from about 250 µg to about 500 µg, from about 500 µg to about 750 µg, from about 750 µg to about 1 mg, or from about 1 mg to about 5 mg.

Those of skill will readily appreciate that dose levels can vary as a function of the specific peptide and/or other factors. Preferred dosages for a given peptide are readily determinable by those of skill in the art by a variety of means. In some embodiments, a single dose of a subject immunomodulatory peptide is administered. In other embodiments, multiple doses of a subject immunomodulatory peptide are administered. Where multiple doses are administered over a period of time, a subject immunomodulatory peptide is administered twice daily (qid), daily (qd), every other day (qod), every third day, three times per week (tiw), or twice per week (biw) over a period of time. For example, a subject immunomodulatory peptide is administered qid, qd, qod, tiw, or biw over a period of from one day to about 2 years or more. For example, a subject immunomodulatory peptide is administered at any of the aforementioned frequencies for one week, two weeks, one month, two months, six months, one year, or two years, or more, depending on various factors.

Anti-L28R Antibody

An anti-IL28R antibody, or a composition comprising the anti-IL28R antibody, when administered in one or more doses to an individual, can modulate an immune response in the individual. Thus, the present disclosure provides methods of modulating an immune response in an individual, the methods generally involving administering to an individual in need thereof an effective amount of an anti-IL28R antibody, e.g., an anti-IL28R antibody present disclosure, or an effective amount of a composition comprising the anti-IL28R antibody. In some cases, the anti-IL28R antibody that is administered increases IL28R signaling. In other cases, the anti-IL28R antibody that is administered blocks (reduces) IL28R signaling.

In some cases, an "effective amount" of an anti-IL28R antibody is an amount that, when administered to an individual in need thereof in one or more doses, increases an immune response in the individual. For example, an "effective amount" of an anti-IL28R antibody can be an amount that, when administered to an individual in need thereof in one or more doses, increases an immune response in the individual by at least about 10%, at least about 25%, at least about 50%, at least about 100% (or 2-fold), at least about 2.5-fold, at least about 5-fold, at least about 10-fold, or more than 10-fold, compared to the level of the immune response in the absence of administration with the anti-IL28R antibody. An immune response can include one or more of: 1) increased B cell proliferation; 2) increased numbers of memory B cells; 4) increased numbers of helper T lymphocytes; 5) increased numbers of memory T cells; 6) increased antibody production; 3) increased numbers of cytotoxic T lymphocytes; 7) increased numbers of dendritic cells, or modulation of dendritic cell function; 8) increased numbers of Th9 cells; 9) increased numbers of any T cell subset (e.g., Th17 T cells; T follicular helper cells; etc.); and 10) decreased numbers of Tregs (T regulatory cells).

In some cases, an "effective amount" of an anti-IL28R antibody is an amount that, when administered to an individual in need thereof in one or more doses, increases a Th2 response in the individual. For example, an "effective amount" of an anti-IL28R antibody can be an amount that, when administered to an individual in need thereof in one or more doses, increases a Th2 response in the individual by at least about 10%, at least about 25%, at least about 50%, at least about 100% (or 2-fold), at least about 2.5-fold, at least about 5-fold, at least about 10-fold, or more than 10-fold, compared to the level of the Th2 response in the absence of administration with the anti-L28R antibody.

In some cases, an "effective amount" of an anti-IL28R antibody is an amount that, when administered to an individual in need thereof in one or more doses, increases the level of a factor (e.g., where the factor is one or more of IL4, IL5, IL9, IL13, IP10, CD40L, fractalkine, GRO, and sIL2R-α) in the individual by at least about 10%, at least about 25%, at least about 50%, at least about 100% (or 2-fold), at least about 2.5-fold, at least about 5-fold, at least about 10-fold, or more than 10-fold, compared to the level of the factor in the individual in the absence of administration with the anti-IL28R antibody.

In some cases, an "effective amount" of an anti-IL28R antibody is an amount that, when administered to an individual in need thereof in one or more doses, increases the level of IL4, IL5, IL9, and IL13 in the individual by at least about 10%, at least about 25%, at least about 50%, at least about 100% (or 2-fold), at least about 2.5-fold, at least about 5-fold, at least about 10-fold, or more than 10-fold, compared to the level of IL4, IL5, IL9, and IL13 in the individual in the absence of administration with the anti-IL28R antibody.

In some cases, an "effective amount" of an anti-IL28R antibody is an amount that, when administered to an individual in need thereof in one or more doses, decreases the level of IL1b and/or IL6 in the individual by at least about 10%, at least about 25%, at least about 50%, at least about 75%, or more than 75%, compared to the level of IL1b and/or IL6 in the individual in the absence of administration with the anti-IL28R antibody.

In some cases, an "effective amount" of an anti-IL28R antibody is an amount that, when administered to an individual in need thereof in one or more doses, increases the level of IFN-α in the individual. For example, an "effective amount" of an anti-IL28R antibody can be an amount that, when administered to an individual in need thereof in one or more doses, increases the IFN-α level in the individual by at least about 10%, at least about 25%, at least about 50%, at least about 100% (or 2-fold), at least about 2.5-fold, at least about 5-fold, at least about 10-fold, or more than 10-fold, compared to the level of IFN-α in the absence of administration with the anti-IL28R antibody.

In some cases, an "effective amount" of an anti-IL28R antibody is an amount that, when administered to an individual in need thereof in one or more doses, increases the level of an anti-inflammatory interferon-stimulated gene (ISG) product in the individual by at least about 10%, at least about 25%, at least about 50%, at least about 100% (or 2-fold), at least about 2.5-fold, at least about 5-fold, at least about 10-fold, or more than 10-fold, compared to the level of the ISG product in the absence of administration with the anti-IL28R antibody. Anti-inflammatory ISG products include, e.g. SOCS1 and Usp18. A "gene product" can be an mRNA and/or a polypeptide.

In some cases, an "effective amount" of an anti-IL28R antibody is an amount that, when administered to an individual in need thereof in one or more doses, reduces the level of a pro-inflammatory ISG product in the individual by at least about 10%, at least about 25%, at least about 50%, at least about 75%, or more than 75%, compared to the pro-inflammatory ISG product in the absence of administration with the anti-IL28R antibody. Pro-inflammatory ISG products include, e.g., MX1, OAS1, IFIT2, ISG15, and the like. A "gene product" can be an mRNA and/or a polypeptide.

In some cases, an "effective amount" of an anti-IL28R antibody is an amount that, when administered to an individual in need thereof in one or more doses, increases the amount of virus-neutralizing antibody in the individual. For example, an "effective amount" of an anti-IL28R antibody can be an amount that, when administered to an individual in need thereof in one or more doses, increases the level of neutralizing antibody to a virus individual by at least about 10%, at least about 25%, at least about 50%, at least about 100% (or 2-fold), at least about 2.5-fold, at least about 5-fold, at least about 10-fold, or more than 10-fold, compared to the level of neutralizing antibody in the absence of administration with the anti-IL28R antibody.

In some cases, an "effective amount" of an anti-IL28R antibody is an amount that, when administered to an individual in need thereof in one or more doses, reduces replication of a virus in the individual. For example, an "effective amount" of an anti-IL28R antibody can be an amount that, when administered to an individual in need thereof in one or more doses, reduces replication of a virus in the individual by at least about 10%, at least about 15%, at least about 20%, at least about 25%, at least about 30%, at least about 40%, at least about 50%, or more than 50%, compared to the level of viral replication in the absence of administration with the anti-IL28R antibody.

Compositions comprising anti-IL28R antibody that are suitable for use in a method of modulating an immune response include a pharmaceutically acceptable excipient, where suitable compositions are as described above in the context of immunostimulatory peptides.

Conventional and pharmaceutically acceptable routes of administration include inhalational (e.g., intranasal), intramuscular, intratracheal, intrathecal, intraperitoneal, subcutaneous, intradermal, transdermal, topical (e.g. to the skin, to the eye, etc.), intravenous, rectal, oral, vaginal, ocular, intraocular, and other enteral and parenteral routes of administration. Routes of administration may be combined, if desired, or adjusted depending upon the antibody and/or the desired effect. An antibody can be administered in a single dose or in multiple doses. In some cases, the route of administration is oral. In some cases, the route of administration is intranasal (e.g., via inhalation). In some cases, the route of administration is subcutaneous (e.g., via injection). In some cases, the route of administration is intradermal (e.g., via injection). In some cases, the route of administration is intramuscular (e.g., via injection).

In some instances, the route of administration and/or mode of administration provides for systemic administration of an anti-IL28R antibody. In other instances, the route of administration and/or mode of administration provides for localized administration of an anti-IL28R antibody. Exemplary routes of administration include oral, intramuscular, subcutaneous, transdermal, intradermal, intranasal, and intravenous routes of administration. As noted above, administration can be by injection, or by implantation of a composition that provides for release of polypeptide such as an antibody.

Although the dosage used will vary depending on the clinical goals to be achieved, a suitable dosage range of an anti-IL28R antibody includes, e.g., from about 1 ng to about 5 mg per unit dose, e.g., from about 1 ng to about 10 ng, from about 10 ng to about 25 ng, from about 25 ng to about 50 ng, from about 50 ng to about 100 ng, from about 100 ng to about 500 ng, from about 500 ng to about 1 µg, from about 1 µg to about 5 µg, from about 5 µg to about 10 µg, from about 10 µg to about 25 µg, from about 25 µg to about 50 µg, from about 50 µg to about 100 µg, from about 100 µg to about 150 µg, from about 150 µg to about 250 µg, from about 250 µg to about 500 µg, from about 500 µg to about 750 µg, from about 750 µg to about 1 mg, or from about 1 mg to about 5 mg.

Those of skill will readily appreciate that dose levels can vary as a function of the specific antibody and/or other factors. Preferred dosages for a given antibody are readily determinable by those of skill in the art by a variety of means. In some embodiments, a single dose of an anti-IL28R antibody is administered. In other embodiments, multiple doses of an anti-IL28R antibody are administered. Where multiple doses are administered over a period of time, an anti-IL28R antibody is administered twice daily (qid), daily (qd), every other day (qod), every third day, three times per week (tiw), or twice per week (biw) over a period of time. For example, an anti-IL28R antibody is administered qid, qd, qod, tiw, or biw over a period of from one day to about 2 years or more. For example, an anti-IL28R antibody is administered at any of the aforementioned frequencies for one week, two weeks, one month, two months, six months, one year, or two years, or more, depending on various factors.

Subjects Suitable for Treatment

Individuals suitable for administration with a peptide, or a peptide composition, of the present disclosure include individuals who are immunosuppressed or immunocompromised; and immunocompetent individuals.

Individuals suitable for administration with a peptide, or a peptide composition, of the present disclosure include immunologically naïve individuals. Individuals suitable for administration with a peptide, or a peptide composition, of the present disclosure include children (e.g., individuals under 21 years of age, under 18 years of age, under the age of 16 years, or under the age of 12 years); elderly individuals (e.g., individuals older than about 65 years, older than about 70 years, or older than 75 years); pregnant women; and individuals having a chronic disease.

Individuals suitable for treatment with a subject method include, e.g., a human, where the human is from about one month to about 6 months, from about 6 months to about 1 year, or from about 1 year to about 5 years of age. Individuals suitable for treatment with a subject method include, e.g., a human, where the human is from about 5 years to about 12 years, from about 13 years to about 18 years, or from about 18 years to about 25 years of age. Individuals suitable for treatment with a subject method include, e.g., a human, where the human is from about 25 years to about 50 years, from about 50 years to about 75 years of age, or older than 75 years of age.

Individuals suitable for treatment with a subject method include, e.g., a human, where the human is immunocompromised. Immunocompromised individuals include, e.g., individuals infected with a human immunodeficiency virus, e.g., where the individual has a lower than normal CD4+ T cell count. The normal range of $CD4^+$ T cell for humans is from about 600 to about 1500 $CD4^+$ T lymphocytes per $mm^3$ blood. Thus, in some embodiments, an immunocompromised individual has a $CD4^+$ T cell count that is less than about 600 $CD4^+$ T cells per $mm^3$ blood.

Immunocompromised individuals include individuals who are immunocompromised as a result of treatment with a cancer chemotherapeutic agent; and individuals who are immunocompromised as a result of radiation therapy (e.g., for the treatment of a cancer). Immunocompromised individuals include individuals who are immunocompromised due to chronic disease, e.g., cancer, diabetes mellitus, rheumatologic diseases (e.g., systemic lupus erythematosus, etc.), immunoglobulin deficiency diseases, and the like. Immunocompromised individuals include transplant recipients (e.g., solid organ transplant recipients (e.g., lung transplant recipients, kidney transplant recipients, etc.); and bone marrow transplant recipients, hematopoietic stem cell transplant recipients, etc.). Immunocompromised individuals include individuals who are immunocompromised as a result of taking certain medications such as steroids, chemotherapeutic agents, TNF-α inhibitors, and the like.

Individuals suitable for treatment with a subject method include individuals who are immunosuppressed, e.g., individuals who are undergoing immunosuppressive treatment, where such individuals include, e.g., transplant recipients. Transplant recipients include, e.g., allograft recipients; xenograft recipients; solid organ transplant recipients (e.g., lung transplant recipients, kidney transplant recipients, etc.); and bone marrow transplant recipients, hematopoietic stem cell transplant recipients, etc.); and the like. Immunosuppressive treatments include, e.g., treatment with a calcineurin inhibitor (e.g., tacrolimus (FK506), cyclosporine, and the like); treatment with an anti-proliferative agent (e.g., sirolimus, mycophenolate, etc.); treatment with drugs such as JAK3 inhibitors; treatment with Belatacept (a fusion protein composed of the Fc fragment of a human IgG1 immunoglobulin linked to the extracellular domain of CTLA-4); induction therapy with T-cell depleting agents; and treatment with immunosuppressive antibody, e.g., Basilixumab.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Generation and Characterization of Immunomodulatory Peptides

Peptides of two different categories were designed:
a) peptides derived from an IFN-λ polypeptide, which peptides block binding of an IFN-λ polypeptide to an IL-28R;
b) peptides derived from an IL-28R, which peptides block binding of an IFN-λ polypeptide to an IL-28R. Peptides in this category included: i) peptides derived from IL-28R1; and ii) peptides derived from IL-10R2.

The peptides are depicted in Tables 1-3. Table 1 provides category (a) peptides; Table 2 provides category (b) peptides; and Table 3 provides category (c) peptides.

TABLE 1 peptides derived from ligand

| Peptide # | Name | Sequence | SEQ ID NO | Length |
|---|---|---|---|---|
| 1 ("28pep1") | IL29-1 | ELASFKKARDALEESLKL | 11 | 18 |
| 2 ("28pep2") | IL28-1 | ELQAFKRAKDALEESLLL | 12 | 18 |
| 3 ("28pep3") | IL29-2 | LKNWSCSSPVFPGN | 21 | 14 |
| 4 ("28pep4") | IL28A-2 | LKDCRCHSRLFPRT | 22 | 14 |
| 5 ("28pep5") | IL28B-2 | LKDCKCRSRLFPRT | 23 | 14 |
| 6 ("28pep6") | IL29-3 | ASVTFNLFRLLTRDLKY | 15 | 17 |
| 7 ("28pep7") | IL28-3 | ASVTFNLFRLLRDLNC | 16 | 17 |

TABLE 2 peptides derived from the IL-28 R

| Peptide # | Name | Sequence | SEQ ID NO | Length |
|---|---|---|---|---|
| 8 ("28pep8") | IL28R-1 | VAYQSSPTRRRWREV | 24 | 15 |
| 9 ("28pep9") | IL28R-2 | MMCLKKQDLYNKFKG | 25 | 15 |
| 10 ("28pep10") | IL28R-3 | SEYLDYLFEVEPAPP | 26 | 15 |
| 11 ("28pep11") | IL28R-4 | NATYQLPPCMPPLDLKY | 27 | 17 |
| 12 ("28pep12") | IL28R-5 | ARTIYTFSVPKYSKF | 28 | 15 |

TABLE 3

| Peptide # | Name | Sequence | SEQ ID NO | Length |
|---|---|---|---|---|
| 13 ("28pep13") | IL28BT-1 | PQELQAFKRAKDALEESL | 29 | 18 |
| 14 ("28pep14") | IL29T-1 | PQELASFKKARDALEESL | 30 | 18 |
| 15 ("28pep15") | IL28BT-2 | LLKDCKCRSRLFPRTWDLRQ | 18 | 20 |
| 16 ("28pep16") | IL28AT-2 | LLKDCRCHSRLFPRTWDLRQ | 19 | 20 |
| 17 ("28pep17") | IL29T-2 | KLKNWSCSSPVFPGNWDLRL | 20 | 20 |
| 18 ("28pep18") | IL28BT-3 | EATADTDPALGDVLDQPL | 31 | 18 |

TABLE 3-continued

| Peptide # | Name | Sequence | SEQ ID NO | Length |
|---|---|---|---|---|
| 19 ("28pep19") | IL28AT-3 | EATADTDPALVDVLDQPL | 32 | 18 |
| 20 ("28pep20") | IL29T-3 | EAAAGPALEDVLDQPL | 33 | 16 |

Table 4 Provides Amino Acid Sequences of Peptides Derived from IL-10R2.

TABLE 4

| Name | Amino acids | sequence | SEQ ID NO: |
|---|---|---|---|
| | 54-70 | ECDFSSLSKYGDHTLRV | 36 |
| | 33-47 | FTAQYLSYRIFQDKC | 37 |
| 10pep1 | | TAQLYSYRIFQDKCM | 38 |
| 10pep2 | | ECDFSSLSKYGDHTLR | 39 |
| 10pep3 | | GMQVEVLADCLHMRFLA | 40 |
| 10pep4 | | QVEVLADCLHMRFLAPKIENE | 41 |
| 10pep5 | | CLHMRFLAPKIENE | 42 |
| 10pep6 | | FLAPKIENEYETWTM | 43 |

Table 5 Provides Amino Acid Sequences of Peptides Derived from IL-29

TABLE 5

| Ligand. amino acids | sequence | SEQ ID NO: |
|---|---|---|
| 5-20 | WTVVLVTLVLGLAVAG | 44 |
| 8-23 | VLVTLVLGLAVAGPVP | 45 |
| 11-25 | TLVLGLAVAGPVPTS | 46 |
| 13-28 | VLGLAVAGPVPTSKPT | 47 |
| 15-32 | GLAVAGPVPTSKPTTTGK | 48 |
| 17-32 | AVAGPVPTSKPTTTGK | 49 |
| 19-33 | AGPVPTSKPTTTGKG | 50 |
| 20-35 | GPVPTSKPTTTGKCH | 51 |
| 24-37 | TSKPTTTGKGCHIG | 52 |
| 25-40 | SKPTTTGKGCHIGRFK | 53 |
| 27-42 | PTTTGKGCHIGRFKSLS | 54 |
| 28-44 | TTTGKGCHIGRFKSLSP | 55 |
| 29-44 | TTGKGCHIGRFKSLSP | 56 |
| 30-45 | TGKGCHIGRFKSLSPQ | 57 |
| 31-46 | GKGCHIGRFKSLSPQE | 58 |
| 32-47 | KGCHIGRFKSLSPQEL | 59 |
| 32-48 | KGCHIGRFXSLSPQELA | 60 |
| 33-49 | GCHIGRFKSLSPQELAS | 61 |
| 34-50 | CHIGRFKSLSPQELASF | 62 |
| 35-51 | HIGRFKSLSPQELASFK | 63 |
| 36-52 | IGRFKSLSPQELASFKK | 64 |
| 110-125 | LEDVLDQPLHTLHHIL | 65 |
| 112-127 | DVLDQPLHTLHHILSQ | 66 |
| 114-129 | LDQPLHTLHHILSQLQ | 67 |
| 116-131 | QPLHTLHHILSQLQAC | 68 |

Table 6 Provides Mouse Peptides

TABLE 6

| Peptide name | sequence | Length |
|---|---|---|
| M28-1 | ELQAFKKAKDAIEKRLLE (SEQ ID NO: 69) | 18 |
| M28-2 | ELQAFKKAKGAIEKRLLE (SEQ ID NO: 70) | 18 |
| M28-6 | DSVTSNLFRLLTRDLKC (SEQ ID NO: 71) | 17 |
| M28-7 | DSVTSNLFQLLLRDLKC (SEQ ID NO: 72) | 17 |
| M28-15-7 | LEKDMRCSSHLISRAWDLKQ (SEQ ID NO: 73) | 20 |
| M28-18a | ENMTDSALATILGQPL (SEQ ID NO: 74) | 16 |
| M28-18b | ENINDSALTTILGQPL (SEQ ID NO: 75) | 16 |
| SM28-1 | KAEKFQLIKKLAEREDLA (SEQ ID NO: 76) | 18 |
| SM28-6 | RRLVTDLSNSLDFCTKL (SEQ ID NO: 77) | 17 |
| SM28-15-7 | KASLLDSRDIQSRHKECLMW (SEQ ID NO: 78) | 20 |
| SM28-18 | PQSMATLGELAILDTN (SEQ ID NO: 79) | 16 |
| MAB3 | VQAASAHGRSPRVESRYLEYLFDVELAPPTLVLTQ (SEQ ID NO: 80) | 35 |
| MAB5 | LFPDTPYGQPVQIPLQQGASRRHCLSARTVYTLIDIKYSQF (SEQ ID NO: 81) | 41 |

Figure 7:
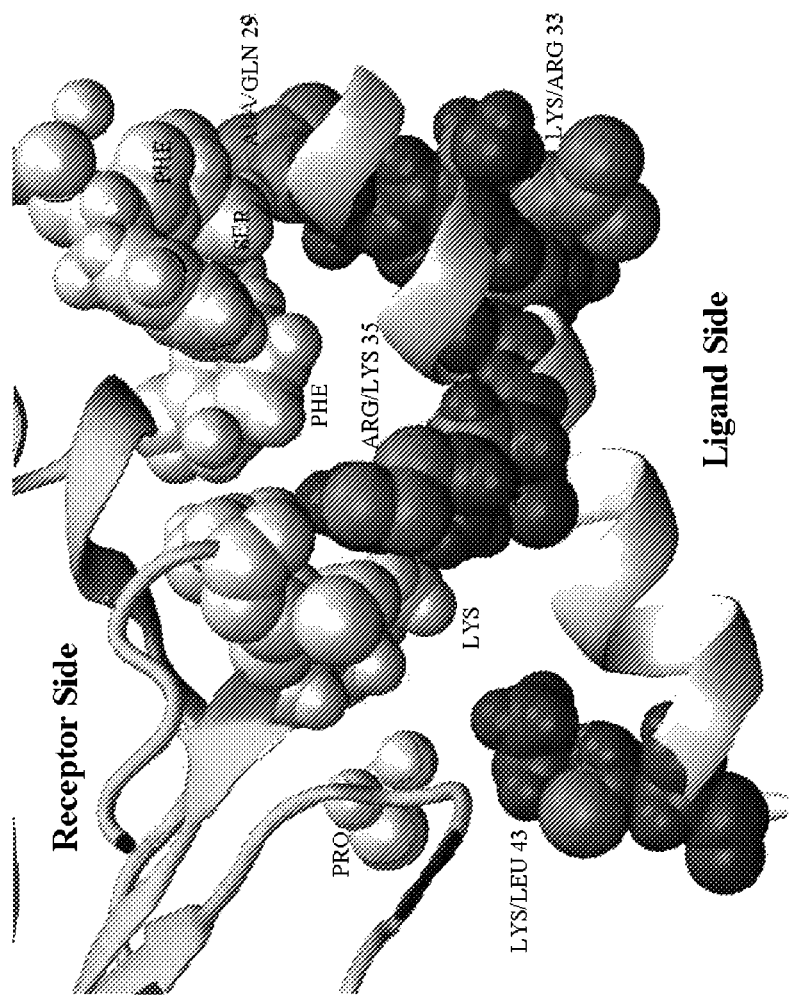
FIG. 7 depicts a comparison between Peptide 1 and Peptide 2.
Figure 8:
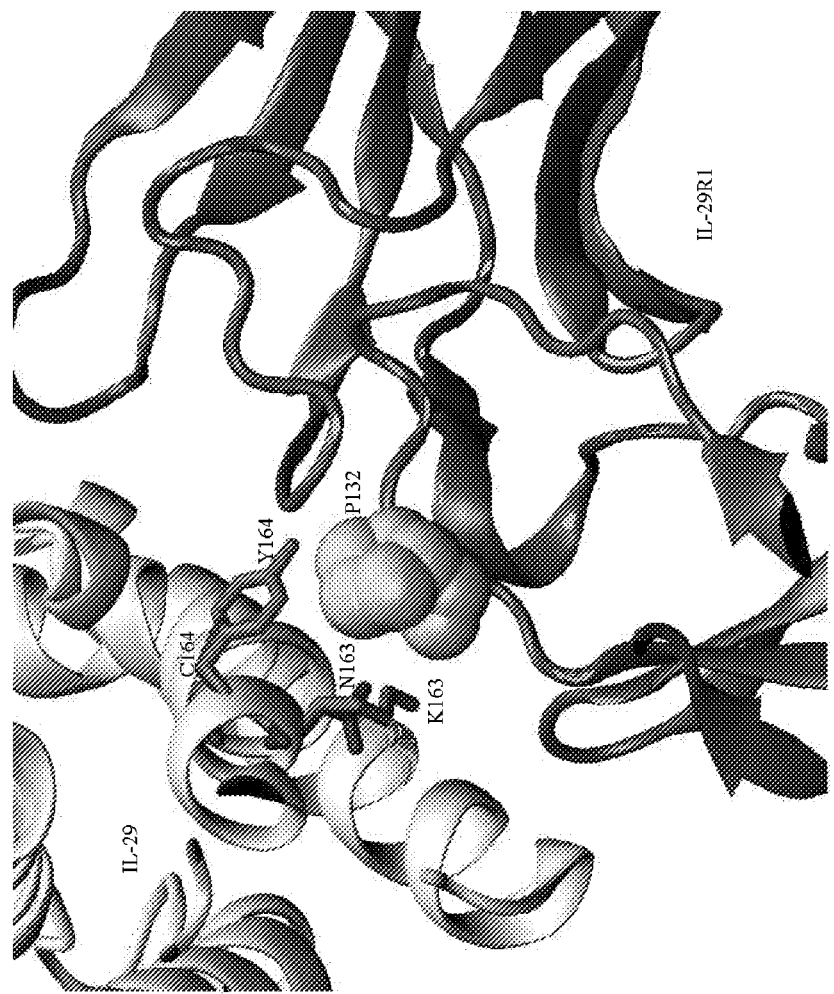
FIG. 8 depicts Peptide 7 and Peptide 8.

As shown in FIG. 7, mutation from Lys43 (Pep1) to Leu43 (Pep2) reduced the possibility for peptide 2 (Pep2) to approach the proline residue on the receptor side. A similar effect is shown for mutation from Arg35 (Pep1) to Lys35 (Pep2), where the arginine residue was able to stack against the lysine and phenylalanine residues on the receptor side. The only difference between peptide 6 ("Pep6"; ASVTFN-LFRLLTRDLKY; SEQ ID NO:15) and peptide 7 ("Pep7"; ASVTFNLFRLLTRDLNC; SEQ ID NO: 16) is two mutations: Y164 (Pep6) to C164 (Pep7) and K163 (Pep6) to N163 (Pep7). As shown in FIG. 8, these two residues on each peptide directly interact with P132 from the receptor side. While Y164 and K163 from peptide 6 form a two-figures shape that holds P132 from the receptor, this interaction is lost in Pep7 due to the mutation. This seems to reduce the binding affinity of Pep7 compared to that of Pep6.

Effect of Peptides on CMV Replication

Peptides were tested for an effect on CMV replication.

The data are depicted in FIG. 1. Peptides 1, 6 and 7 show strong inhibitory effects at day 4 and day 6 in a plaque assay. HFF-1 cells were pre-treated for 2 h with peptides (10 µM), then washed and infected with CMV (Towne strain, MOI 0.03) and viral growth curves were generated.

Effect of Peptides on Influenza Virus-induced IgG Production

Figure 2:
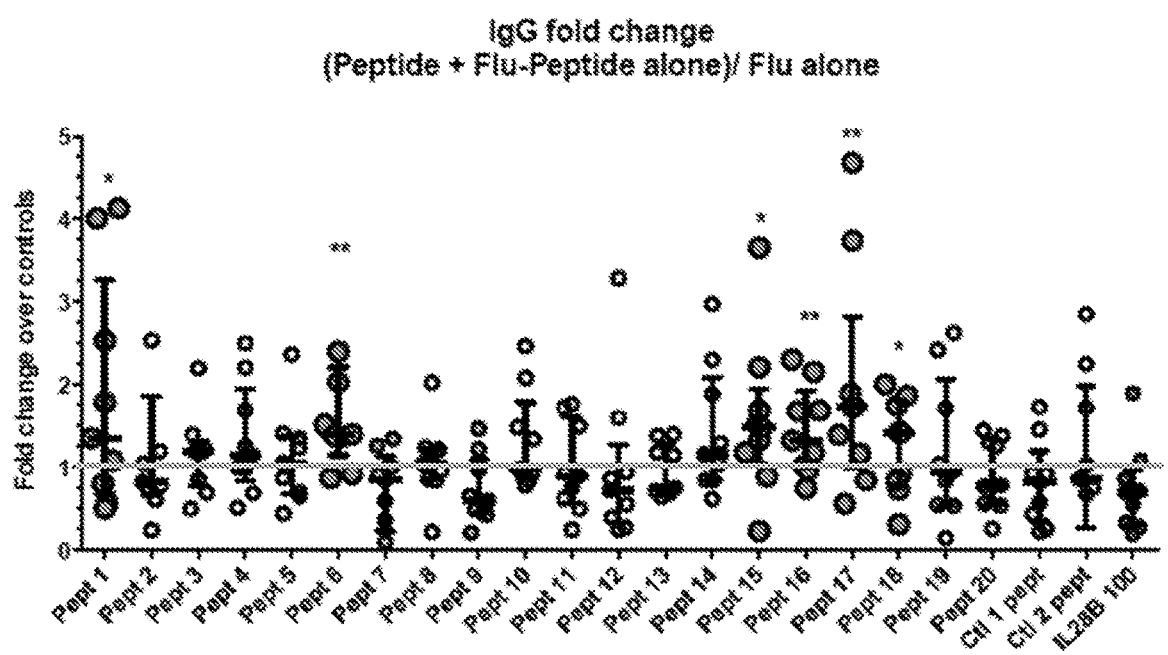
FIG. 2 depicts boosting effects of peptides on influenza virus-induced IgG production.

Peptides were tested for an effect on the level of influenza virus-induced IgG production. The data are depicted in FIG. 2. Boosting effects of peptides on Influenza induced IgG production. PBMCs from healthy donors were pre-treated for 2 h with peptides (10 µM) and stimulated with Influenza H1N1 for 7 days.

Example 2

Further Characterization of Peptides

The effect of various peptides listed in Tables 1-3 on binding was assessed.

Figure 9:
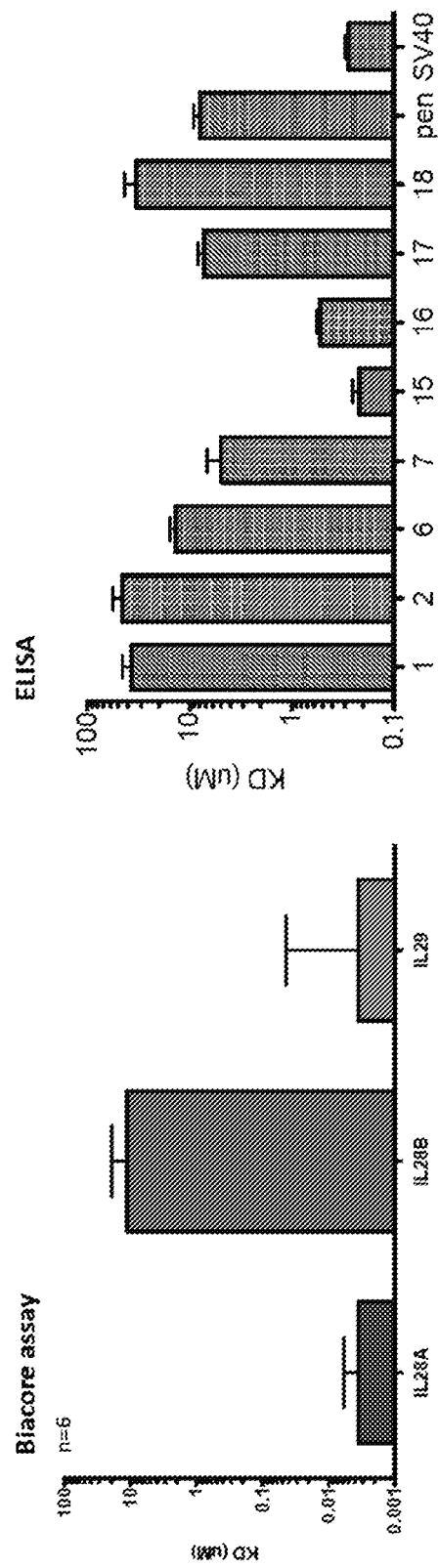
FIG. 9 depicts binding affinity ($K_D$ values in μM) of ligands IL28A, IL28B, and IL29, and of peptides 1, 2, 6, 7, and 15-18, for IL28R1.

FIG. 9 depicts binding affinity ($K_D$ values in PM) of ligands IL28A, IL28B, and IL29, and of peptides 1, 2, 6, 7, and 15-18, for IL28R1. Biacore assay indicates a significant lower binding affinity of IL28B towards IL28R1 (left). In ELISA assays, the $K_D$ values indicate differences between peptides. The control peptide SV40 showed unspecific binding to the IL28R1 (right).

Figure 10:
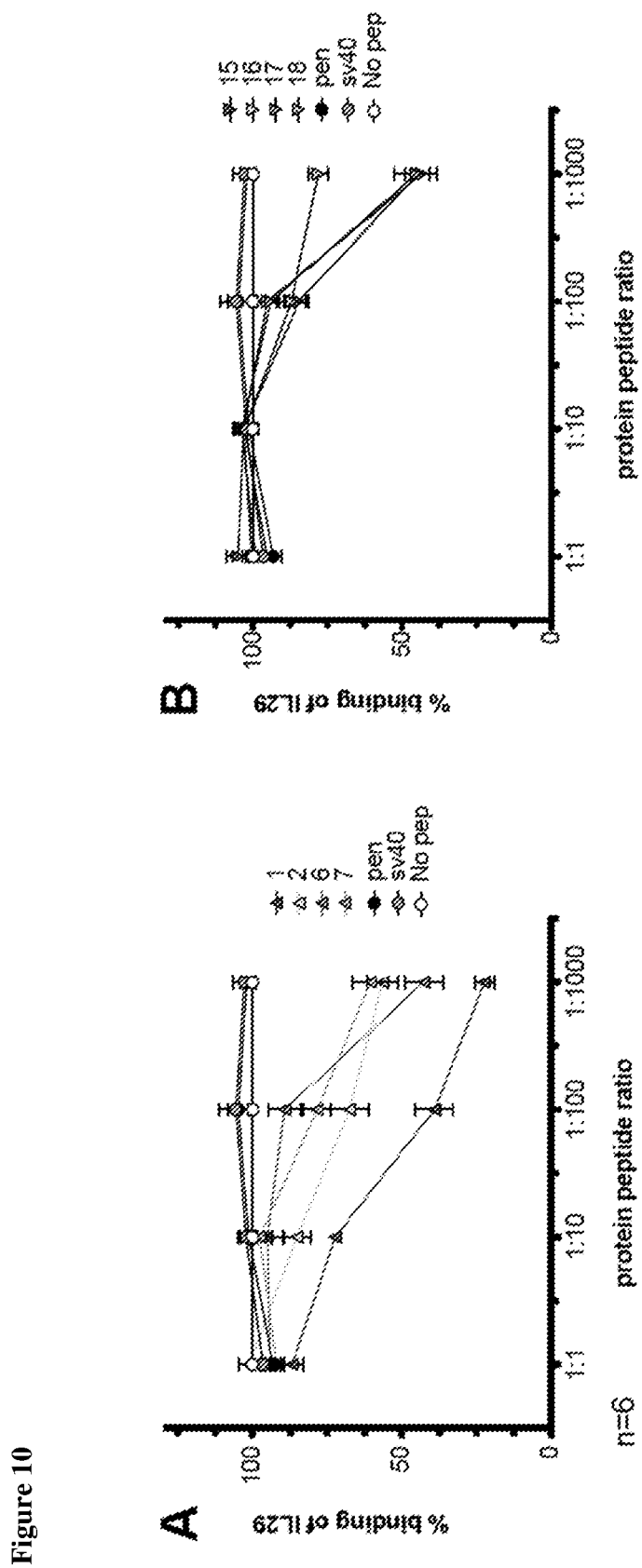
FIGS. 10A and 10B depict the effect of peptides on binding of IL29 to IL-28R.

FIG. 10 depicts the effect of peptides on binding of IL29 to IL-28R. Binding of IL29 was disrupted by addition of increasing peptide concentrations. ELISA assay showed that the peptide 1 and 6 were highly potent in inhibiting the binding of IL29. IL29 was chosen, because it had the highest binding affinity of all Interferon lambdas using a Biacore assay. Peptide 1 for example showed a IC50 in only 50 time excess of peptide over the natural ligand. FIG. 10A shows peptide 1, 2, 6 and 7. FIG. 10B shows peptide 15, 16, 17 and 18. Several control peptides were included, which control peptides did not show an inhibition of the binding.

Figure 11:
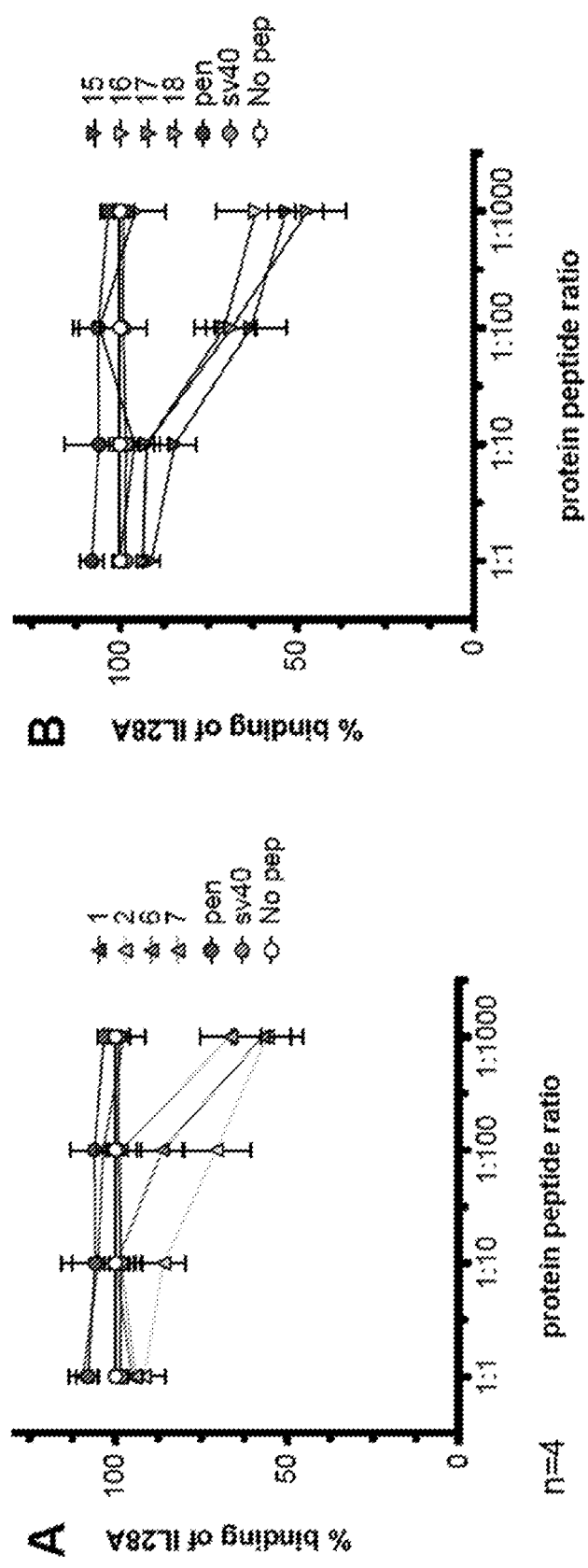
FIGS. 11A and 11B depict the effect of peptides on binding of IL28A to IL-28R.

FIG. 11 depicts the effect of peptides on binding of IL28A to IL-28R. Binding of IL29 was disrupted by addition of increasing peptide concentrations. ELISA assay showed that the peptide 1 and 6 were highly potent in inhibiting the binding of IL29. IL29 was chosen, because it had the highest binding affinity of all Interferon lambdas using a Biacore assay. Peptide 1 for example showed an IC50 in only 50 time excess of peptide over the natural ligand. FIG. 11A shows peptide 1, 2, 6 and 7. FIG. 11B shows peptide 15, 16, 17 and 18. Several control peptides were included, which control peptides did not show an inhibition of the binding.

FIGS. 11A and 11B. Binding of IL28A was disrupted by addition of increasing peptide concentrations. ELISA assay showed that peptides 15, 16, and 17 were potent in inhibiting the binding of IL28A. FIG. 11A shows the effect of peptides 1, 2, 6, and 7. FIG. 11B shows the effect of peptides 15, 16, 17, and 18. Control peptides "pen" and "sv40" did not inhibit binding.

Example 3

Generation of Anti-IL28R Antibodies

Anti-IL28R antibodies were generated. FIG. 12 depicts amino acid sequences of peptides used to generate antibodies to IL-28R.

Example 4

Effect of Immunomodulatory Peptides on Macrophage Function

The effect of peptide 1 and peptide 17 on STAT-1 phosphorylation in macrophages was tested using flow cytometry.

STAT1 phosphorylation is one of the earliest events that occur after the IFN receptor is activated. THP1 cells (a monocytic cell line) were stimulated for 3 days with phorbol-12-myristate-13-acetate (PMA) and then rested for another 5 days in standard cultivation methods (37° C. 5% CO2) with RPMI containing 10% fetal calf serum (FCS). After 3 days, the PMA was removed and fresh media added. This treatment induces maturation of THP1, such that the THP1 cells are induced to express macrophage markers (Daigneault et al. (2010) *PLoSOne* 5:e8668). Next, the cells were treated: (i) either for 90 min with peptide 1 at a concentration of 10 µM and then added IL28B at 100 ng/mL or (ii) peptide 17 was added directly together with IL28B. "Scramble p1" is a control peptide with the amino acid sequence of p1 scrambled. Scramble p17" is a control peptide with the amino acid sequence of p17 scrambled.

Figure 15:
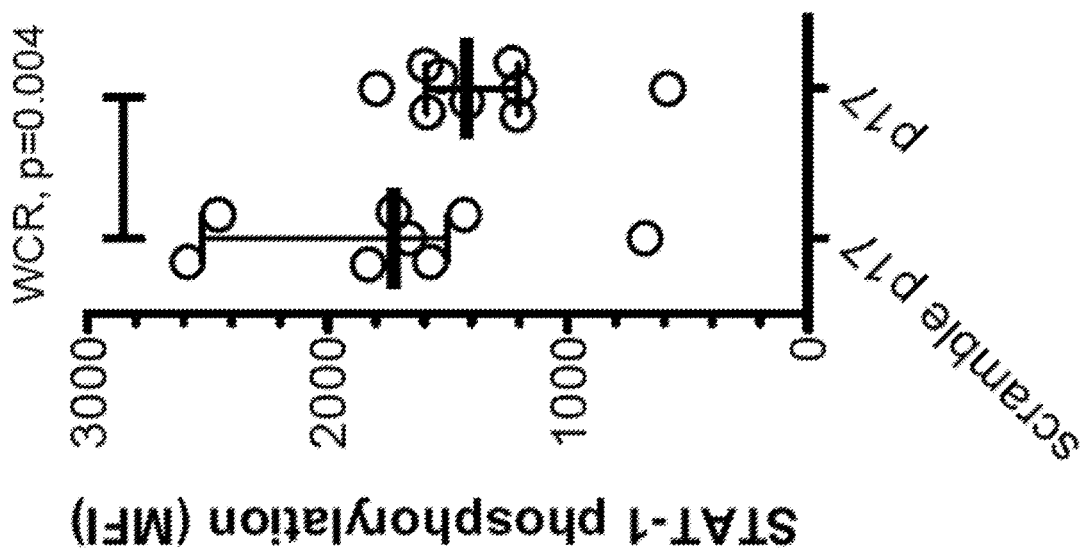
FIG. 15 depicts the effect of peptide 17 ("p17") on STAT-1 phosphorylation in THP1-derived macrophages.
Figure 14:
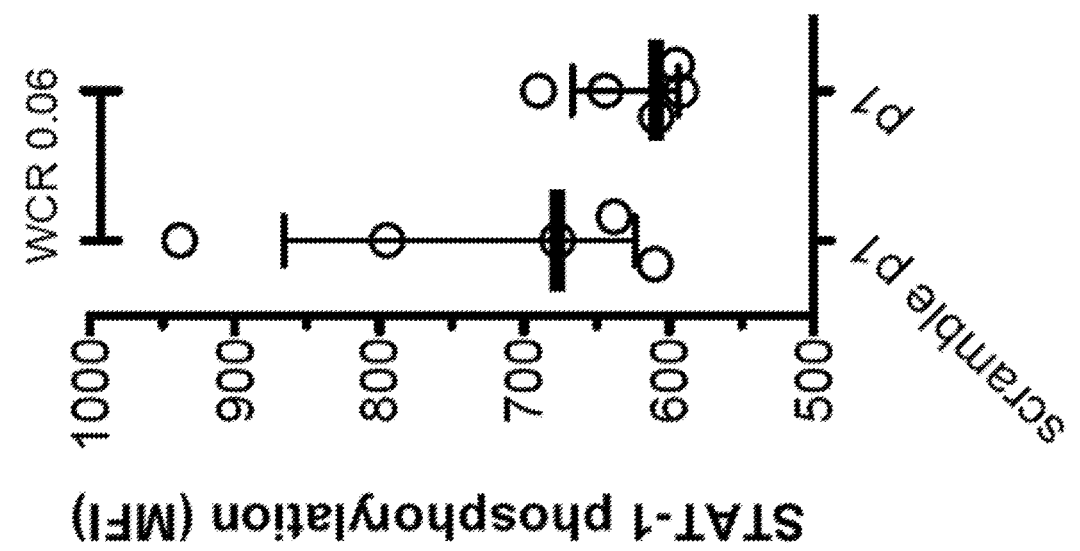
FIG. 14 depicts the effect of peptide 1 ("p1") on STAT-1 phosphorylation in THP1-derived macrophages.

The data are depicted in FIGS. 14 and 15. The results indicate that peptide 1 (FIG. 14) and peptide 17 (FIG. 15) reduce STAT1 phosphorylation.

Example 5

Effect of Immunomodulatory Peptides on B Cell Function

The effect of a mixture of immunomodulatory peptides on B cell function was tested.

Patient population. A cohort of immunosuppressed adult solid organ transplant recipients was used for this study. Healthy non-immunosuppressed non-vaccinated volunteers (HV) were recruited as controls. Peripheral blood mononuclear cells (PBMCs) from 47 transplant recipients were available. The study protocols were approved through the University of Alberta research ethics board and written informed consent was obtained from all participants.

Influenza viruses. For immune stimulation, a formalin inactivated, partially purified A/California/7/2009 (H1N1) (NIBSC, NXMC-X179A, UK) was used. The H1N1 stock contained 50 µg/mL of hemagglutinin protein and was re-constituted in PBS. For all experiments a final concentration of 0.3 µg/mL was used.

IgG ELISA for influenza-induced antibodies. Cell-free supernatants were collected from PBMC cultures at indicated time points and stored at −80° C., until analysis. An in-house human IgG ELISA assay was developed using antibodies and human IgG standard. In brief, 96 well EIA/RIA plates (Costar) were coated overnight with donkey anti-human IgG antibody at 5 µg/ml. Plates were washed with PBS/0.05% Tween and supernatant samples (diluted 1:5) or ChromPure Human IgG standard (Jackson Immunoresearch) were added in duplicate for 2 hrs at room temperature. After washing extensively, detection antibody (goat anti-human IgG alkaline phosphatase, 1:15,000) was added for 1 hr at room temperature. After washing. PNPP substrate was added and the plate was read every 5 min at 405 nm with correction at 570 nm.

PBMCs were obtained from transplant recipients just prior to vaccination against H1N1. PBMCs were incubated with a mixture of peptide 6 (ASVTFNLFRLLTRDLNC;

SEQ ID NO:16), peptide 16 (LLKDCRCHSRLF-PRTWDLRQ; SEQ ID NO:19), and peptide 17 (KLKN-WSCSSPVFPGNWDLRL; SEQ ID NO:20) for 2 hours. The PBMCs were then stimulated with H1N1 overnight. The following day, B cell activation markers were determined using flow cytometry. HIN-stimulated IgG secreted by B cells was determined by ELISA after a 5-day stimulation. The data are shown in FIGS. 16 and 17.

Figure 16:
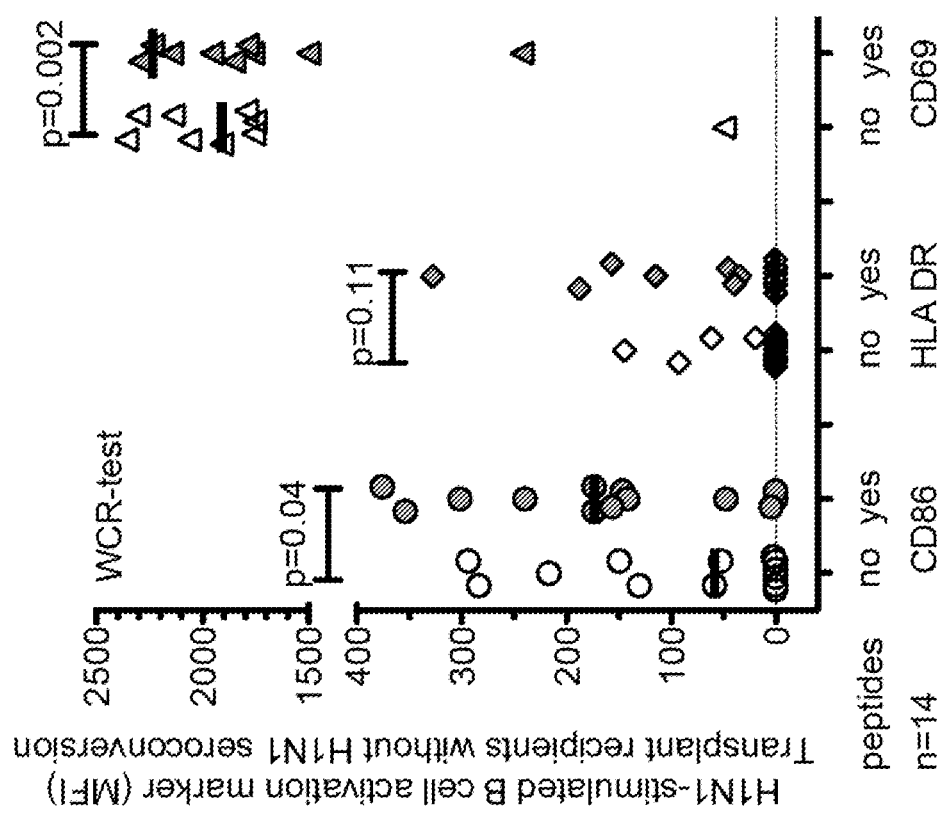
FIG. 16 depicts the effect of a mixture of peptide 6, peptide 16, and peptide 17 on expression, on PBMCs from transplant recipients, of markers for co-stimulatory activation and antigen presentation.

The mean fluorescence intensity (MFI) for CD86, HLA-DR, and CD69 on B cells is shown in FIG. 16. The MFI correlates with the amount of molecule expressed on the cell surface. The combination of peptides 6, 16, and 17 prior to H1N1 stimulation increased the expression of H1N1-stimulated B-cell activation markers CD86, HLA-DR, and CD69.

Figure 17:
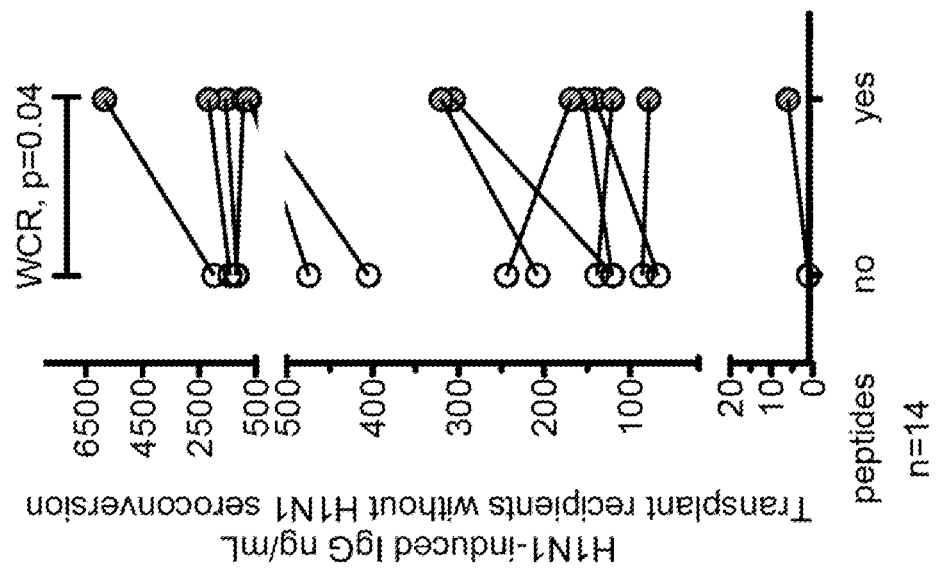
FIG. 17 depicts the effect of a mixture of peptide 6, peptide 16, and peptide 17 on H1N1-induced IgG secretion by PBMCs from transplant recipients.

The amount of H1N1-stimulated IgG secreted by B cells is shown in FIG. 17. The combination of peptides 6, 16, and 17 prior to H1N1 stimulation increased H1N1-stimulated IgG production compared to peptide controls.

Example 6

Figure 20:
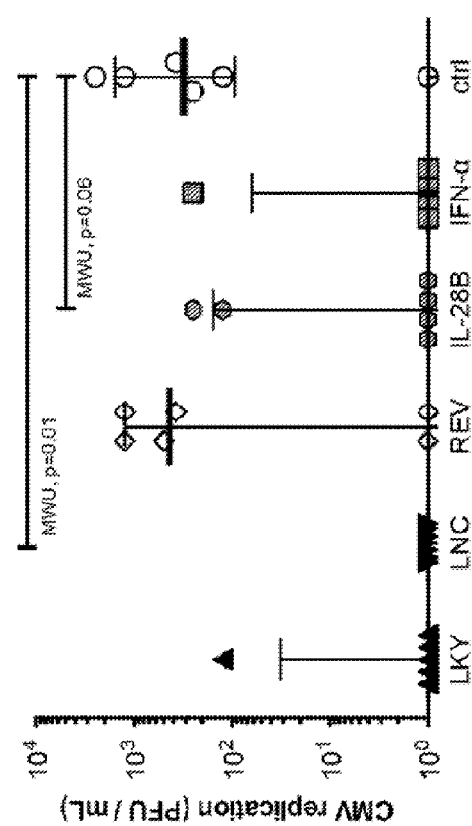
FIG. 20 depicts the effect of various peptides on CMV replication in HFF1 cells.
Figure 19:
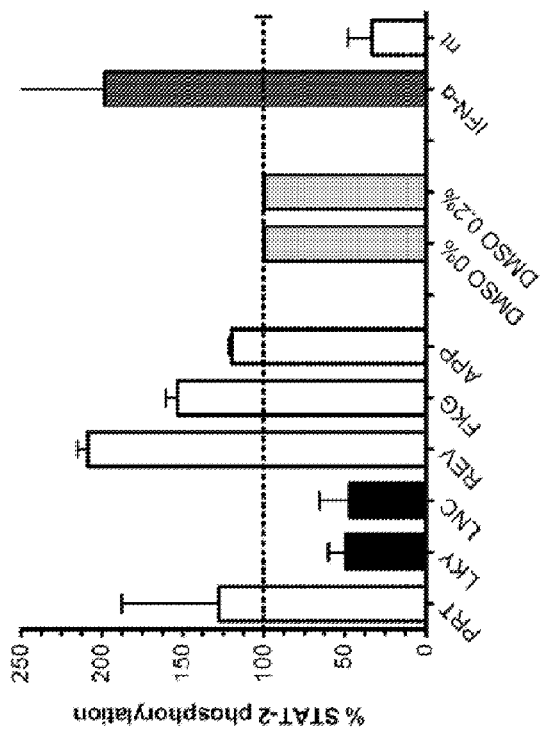
FIG. 19 depicts the effect of various peptides on STAT-2 phosphorylation in HFF1 cells.

Effect of Immunomodulatory Peptides on STAT2 Phosphorylation and on CMV Replication Peptides PRT (LKDCKCRSRLFPRT; SEQ ID NO:23), LKY (ASVTFNLFRLLTRDLKY; SEQ ID NO: 15), and LNC (ASVTFNLFRLLTRDLNC; SEQ ID NO: 16) were pre-incubated at a concentration of 10 µM with HFF-1 cells (ATCC HS97FS. SCRC1041, and CCD1112SK). The cells were washed, then challenged with IL-28B (100 ng/ml) for 30 minutes. Peptides REV (VAYQSSPTRRRWREV; SEQ ID NO:24), FKG (MMCLKKQDLYNKFKG; SEQ ID NO:25), and APP (SEYLDYLFEVEPAPP; SEQ ID NO:26) were pre-incubated for 2 hours with IL-28B, then added to HFF1 for 30 minutes. Proteins were harvested and STAT2 phosphorylation was determined by Western blot analysis. The effect of the peptides on CMV replication in HFF-1 cells was also tested. HFF-1 cells were pre-treated for 2 hours with peptides (10 µM) or control. CMV replication was determined 4 days later using plaque assays. The data are depicted in FIGS. 19 and 20. In FIG. 19, the data are from Western blot experiments. HFF11 cells were pre-treated with individual peptides for 2 hours, then challenged with IL28B for 30 minutes. Results were normalized to STAT2 and β-tubulin baseline expression. In FIG. 20, the data are from plaque assays. HFF1 cells were pre-treated with individual peptides for 2 hours, then infected with CMV Towne strain (multiplicity of infection 0.03). Plaque forming units (PFU) at day 4 were determined.

As shown in FIG. 19, peptides LKY and LNC led to a 40% and 34% reduction in STAT2-phosphorylation respectively. None of peptides REV, FKG, and APP blocked STAT-2 phosphorylation. As shown in FIG. 20, and consistent with the ability to inhibit signalling by IL-28B, pre-treatment of HFF-1 cells with peptide LNC resulted in 2.5 $\log_{10}$ lower CMV replication at day 4 after infection.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising:
   an isolated peptide that comprises an amino acid sequence selected from:
   a) LLKDCKCRSRLFPRTWDLRQ (SEQ ID NO:18);
   b) LLKDCRCHSRLFPRTWDLRQ (SEQ ID NO:19); and
   c) KLKNWSCSSPVFPGNWDLRL (SEQ ID NO:20),
   wherein the isolated peptide modulates an immune response to an influenza virus in an individual, and wherein the isolated peptide has a length of 20 amino acids; and
   an immune-stimulating amount of an adjuvant.

2. The composition of claim 1, wherein the peptide comprises a non-peptide isosteric linkage.

3. The composition of claim 1, wherein the peptide comprises at least one non-encoded amino acid.

4. The composition of claim 3, wherein the non-encoded amino acid is a D-amino acid.

5. The composition of claim 1, further comprising a pathogen or a pathogen component.

6. The composition of claim 5, wherein the pathogen is a live attenuated virus, an inactivated virus, a split virus, a virus subunit, or a nucleic acid comprising a nucleotide sequence encoding a virus subunit.

7. The composition of claim 6, wherein the virus is an influenza virus.

8. The composition of claim 6, wherein the virus is a member of Herpesviridae.

9. A method of increasing an immune response in an individual, the method comprising administering to an individual in need thereof an effective amount of a composition of claim 1.

10. The method of claim 9, wherein the individual is a human.

11. The method of claim 10, wherein the individual is immunocompromised.

12. The method of claim 9, wherein said administering is via intramuscular injection, intradermal injection, subcutaneous injection, or via inhalation.

13. A method of modulating a cellular response in vitro or ex vivo, the method comprising contacting a cell or a cell population in vitro or ex vivo with a composition of claim 1, wherein said contacting modulates a cellular response.

14. The method of claim 13, wherein the cellular response comprises proliferation, cytokine production, or immunoglobulin production.

15. A method of modulating an immune response in an individual, the method comprising administering to an individual in need thereof an effective amount of a composition of claim 1 that inhibits binding of an IFN-λ polypeptide to an IL-28R.

* * * * *

SEQUENCE LISTING

```
<160> NUMBER OF SEQ ID NOS: 109

<210> SEQ ID NO 1
<211> LENGTH: 200
<212> TYPE: PRT
<213> ORGANISM: Homo sapiens

<400> SEQUENCE: 1

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140
```

```
Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
        195                 200

<210> SEQ ID NO 2
<211> LENGTH: 200
<212> TYPE: PRT
<213> ORGANISM: Homo sapiens

<400> SEQUENCE: 2

Met Lys Leu Asp Met Thr Gly Asp Cys Thr Pro Val Leu Val Leu Met
1               5                   10                  15

Ala Ala Val Leu Thr Val Thr Gly Ala Val Pro Val Ala Arg Leu His
                20                  25                  30

Gly Ala Leu Pro Asp Ala Arg Gly Cys His Ile Ala Gln Phe Lys Ser
            35                  40                  45

Leu Ser Pro Gln Glu Leu Gln Ala Phe Lys Arg Ala Lys Asp Ala Leu
50                  55                  60

Glu Glu Ser Leu Leu Lys Asp Cys Arg Cys His Ser Arg Leu Phe
65                  70                  75                  80

Pro Arg Thr Trp Asp Leu Arg Gln Leu Gln Val Arg Glu Arg Pro Met
                85                  90                  95

Ala Leu Glu Ala Glu Leu Ala Leu Thr Leu Lys Val Leu Glu Ala Thr
            100                 105                 110

Ala Asp Thr Asp Pro Ala Leu Val Asp Val Leu Asp Gln Pro Leu His
            115                 120                 125

Thr Leu His His Ile Leu Ser Gln Phe Arg Ala Cys Ile Gln Pro Gln
130                 135                 140

Pro Thr Ala Gly Pro Arg Thr Arg Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Leu Asn Cys
            180                 185                 190

Val Ala Ser Gly Asp Leu Cys Val
            195                 200

<210> SEQ ID NO 3
<211> LENGTH: 196
<212> TYPE: PRT
<213> ORGANISM: Homo sapiens

<400> SEQUENCE: 3

Met Thr Gly Asp Cys Met Pro Val Leu Val Leu Met Ala Ala Val Leu
1               5                   10                  15

Thr Val Thr Gly Ala Val Pro Val Ala Arg Leu Arg Gly Ala Leu Pro
                20                  25                  30

Asp Ala Arg Gly Cys His Ile Ala Gln Phe Lys Ser Leu Ser Pro Gln
            35                  40                  45

Glu Leu Gln Ala Phe Lys Arg Ala Lys Asp Ala Leu Glu Glu Ser Leu
50                  55                  60
```

```
Leu Leu Lys Asp Cys Lys Cys Arg Ser Arg Leu Phe Pro Arg Thr Trp
 65                  70                  75                  80

Asp Leu Arg Gln Leu Gln Val Arg Glu Arg Pro Val Ala Leu Glu Ala
                 85                  90                  95

Glu Leu Ala Leu Thr Leu Lys Val Leu Glu Ala Thr Ala Asp Thr Asp
            100                 105                 110

Pro Ala Leu Gly Asp Val Leu Asp Gln Pro Leu His Thr Leu His His
        115                 120                 125

Ile Leu Ser Gln Leu Arg Ala Cys Ile Gln Pro Gln Pro Thr Ala Gly
    130                 135                 140

Pro Arg Thr Arg Gly Arg Leu His His Trp Leu His Arg Leu Gln Glu
145                 150                 155                 160

Ala Pro Lys Lys Glu Ser Pro Gly Cys Leu Glu Ala Ser Val Thr Phe
                165                 170                 175

Asn Leu Phe Arg Leu Leu Thr Arg Asp Leu Asn Cys Val Ala Ser Gly
            180                 185                 190

Asp Leu Cys Val
        195

<210> SEQ ID NO 4
<211> LENGTH: 520
<212> TYPE: PRT
<213> ORGANISM: Homo sapiens

<400> SEQUENCE: 4

Met Ala Gly Pro Glu Arg Trp Gly Pro Leu Leu Leu Cys Leu Leu Gln
  1               5                  10                  15

Ala Ala Pro Gly Arg Pro Arg Leu Ala Pro Pro Gln Asn Val Thr Leu
                 20                  25                  30

Leu Ser Gln Asn Phe Ser Val Tyr Leu Thr Trp Leu Pro Gly Leu Gly
             35                  40                  45

Asn Pro Gln Asp Val Thr Tyr Phe Val Ala Tyr Gln Ser Ser Pro Thr
         50                  55                  60

Arg Arg Arg Trp Arg Glu Val Glu Glu Cys Ala Gly Thr Lys Glu Leu
 65                  70                  75                  80

Leu Cys Ser Met Met Cys Leu Lys Lys Gln Asp Leu Tyr Asn Lys Phe
                 85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
        115                 120                 125

Val Leu Val Leu Thr Gln Thr Glu Glu Ile Leu Ser Ala Asn Ala Thr
    130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
        195                 200                 205

Tyr Ser Lys Phe Ser Lys Pro Thr Cys Phe Leu Leu Glu Val Pro Glu
    210                 215                 220

Ala Asn Trp Ala Phe Leu Val Leu Pro Ser Leu Leu Ile Leu Leu Leu
225                 230                 235                 240
```

```
Val Ile Ala Ala Gly Gly Val Ile Trp Lys Thr Leu Met Gly Asn Pro
            245                 250                 255

Trp Phe Gln Arg Ala Lys Met Pro Arg Ala Leu Asp Phe Ser Gly His
        260                 265                 270

Thr His Pro Val Ala Thr Phe Gln Pro Ser Arg Pro Glu Ser Val Asn
        275                 280                 285

Asp Leu Phe Leu Cys Pro Gln Lys Glu Leu Thr Arg Gly Val Arg Pro
        290                 295                 300

Thr Pro Arg Val Arg Ala Pro Ala Thr Gln Gln Thr Arg Trp Lys Lys
305                 310                 315                 320

Asp Leu Ala Glu Asp Glu Glu Glu Asp Glu Asp Thr Glu Asp
                325                 330                 335

Gly Val Ser Phe Gln Pro Tyr Ile Glu Pro Pro Ser Phe Leu Gly Gln
            340                 345                 350

Glu His Gln Ala Pro Gly His Ser Glu Ala Gly Gly Val Asp Ser Gly
        355                 360                 365

Arg Pro Arg Ala Pro Leu Val Pro Ser Glu Gly Ser Ser Ala Trp Asp
        370                 375                 380

Ser Ser Asp Arg Ser Trp Ala Ser Thr Val Asp Ser Ser Trp Asp Arg
385                 390                 395                 400

Ala Gly Ser Ser Gly Tyr Leu Ala Glu Lys Gly Pro Gly Gln Gly Pro
                405                 410                 415

Gly Gly Asp Gly His Gln Glu Ser Leu Pro Pro Glu Phe Ser Lys
        420                 425                 430

Asp Ser Gly Phe Leu Glu Glu Leu Pro Glu Asp Asn Leu Ser Ser Trp
        435                 440                 445

Ala Thr Trp Gly Thr Leu Pro Pro Glu Pro Asn Leu Val Pro Gly Gly
450                 455                 460

Pro Pro Val Ser Leu Gln Thr Leu Thr Phe Cys Trp Glu Ser Ser Pro
465                 470                 475                 480

Glu Glu Glu Glu Glu Ala Arg Glu Ser Glu Ile Glu Asp Ser Asp Ala
                485                 490                 495

Gly Ser Trp Gly Ala Glu Ser Thr Gln Arg Thr Glu Asp Arg Gly Arg
            500                 505                 510

Thr Leu Gly His Tyr Met Ala Arg
        515                 520

<210> SEQ ID NO 5
<211> LENGTH: 38
<212> TYPE: PRT
<213> ORGANISM: Artificial Sequence
<220> FEATURE:
<223> OTHER INFORMATION: Synthetic amino acid sequence

<400> SEQUENCE: 5

Gly Pro Leu Leu Cys Leu Leu Gln Ala Ala Pro Gly Arg Pro Arg
1               5                   10                  15

Leu Ala Pro Pro Gln Asn Val Thr Leu Leu Ser Gln Asn Phe Ser Val
            20                  25                  30

Tyr Leu Thr Trp Leu Pro
        35

<210> SEQ ID NO 6
<211> LENGTH: 39
<212> TYPE: PRT
<213> ORGANISM: Artificial sequence
```

-continued

```
<220> FEATURE:
<223> OTHER INFORMATION: Synthetic amino acid sequence

<400> SEQUENCE: 6

Asp Val Thr Tyr Phe Val Ala Tyr Gln Ser Ser Pro Thr Arg Arg Arg
1               5                   10                  15

Trp Arg Glu Val Glu Glu Cys Ala Gly Thr Lys Glu Leu Leu Cys Ser
            20                  25                  30

Met Met Cys Leu Lys Lys Gln
        35

<210> SEQ ID NO 7
<211> LENGTH: 35
<212> TYPE: PRT
<213> ORGANISM: Artificial sequence
<220> FEATURE:
<223> OTHER INFORMATION: Synthetic amino acid sequence

<400> SEQUENCE: 7

Val Arg Thr Val Ser Pro Ser Ser Lys Ser Pro Trp Val Glu Ser Glu
1               5                   10                  15

Tyr Leu Asp Tyr Leu Phe Glu Val Glu Pro Ala Pro Pro Val Leu Val
            20                  25                  30

Leu Thr Gln
        35

<210> SEQ ID NO 8
<211> LENGTH: 24
<212> TYPE: PRT
<213> ORGANISM: Artificial sequence
<220> FEATURE:
<223> OTHER INFORMATION: Synthetic amino acid sequence

<400> SEQUENCE: 8

Ser Ala Asn Ala Thr Tyr Gln Leu Pro Pro Cys Met Pro Pro Leu Asp
1               5                   10                  15

Leu Lys Tyr Glu Val Ala Phe Trp
            20

<210> SEQ ID NO 9
<211> LENGTH: 41
<212> TYPE: PRT
<213> ORGANISM: Artificial sequence
<220> FEATURE:
<223> OTHER INFORMATION: Synthetic amino acid sequence

<400> SEQUENCE: 9

Leu Phe Pro Val Thr Pro His Gly Gln Pro Val Gln Ile Thr Leu Gln
1               5                   10                  15

Pro Ala Ala Ser Glu His His Cys Leu Ser Ala Arg Thr Ile Tyr Thr
            20                  25                  30

Phe Ser Val Pro Lys Tyr Ser Lys Phe
        35                  40

<210> SEQ ID NO 10
<211> LENGTH: 18
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (3)..(3)
<223> OTHER INFORMATION: the amino acid at this position can be an A or
```

```
                                                Q
<220> FEATURE:
<221> NAME/KEY: MISC_FEATURE
<222> LOCATION: (4)..(4)
<223> OTHER INFORMATION: the amino acid at this position can be an S or
      A
<220> FEATURE:
<221> NAME/KEY: MISC_FEATURE
<222> LOCATION: (7)..(7)
<223> OTHER INFORMATION: the amino acid at this position can be a K or
      R
<220> FEATURE:
<221> NAME/KEY: MISC_FEATURE
<222> LOCATION: (9)..(9)
<223> OTHER INFORMATION: the amino acid at this position can be an R or
      K
<220> FEATURE:
<221> NAME/KEY: MISC_FEATURE
<222> LOCATION: (17)..(17)
<223> OTHER INFORMATION: the amino acid at this position can be an L or
      K

<400> SEQUENCE: 10

Glu Leu Xaa Xaa Phe Lys Xaa Ala Xaa Asp Ala Leu Glu Glu Ser Leu
1               5                   10                  15

Xaa Leu

<210> SEQ ID NO 11
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 11

Glu Leu Ala Ser Phe Lys Lys Ala Arg Asp Ala Leu Glu Glu Ser Leu
1               5                   10                  15

Lys Leu

<210> SEQ ID NO 12
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 12

Glu Leu Gln Ala Phe Lys Arg Ala Lys Asp Ala Leu Glu Glu Ser Leu
1               5                   10                  15

Leu Leu

<210> SEQ ID NO 13
<211> LENGTH: 17
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (16)..(16)
<223> OTHER INFORMATION: the amino acid at this position can be a K or N
<220> FEATURE:
<221> NAME/KEY: MISC_FEATURE
<222> LOCATION: (17)..(17)
<223> OTHER INFORMATION: the amino acid at this position can be a Y or C

<400> SEQUENCE: 13

Ala Ser Val Thr Phe Asn Leu Phe Arg Leu Leu Thr Arg Asp Leu Xaa
1               5                   10                  15
```

```
<210> SEQ ID NO 14
<211> LENGTH: 20
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: the amino acid at this position can be an L or
      K
<220> FEATURE:
<221> NAME/KEY: MISC_FEATURE
<222> LOCATION: (4)..(4)
<223> OTHER INFORMATION: the amino acid at this position can be a D or N
<220> FEATURE:
<221> NAME/KEY: MISC_FEATURE
<222> LOCATION: (5)..(5)
<223> OTHER INFORMATION: the amino acid at this position can be a C or W
<220> FEATURE:
<221> NAME/KEY: MISC_FEATURE
<222> LOCATION: (6)..(6)
<223> OTHER INFORMATION: the amino acid at this position can be a K, R,
      or S
<220> FEATURE:
<221> NAME/KEY: MISC_FEATURE
<222> LOCATION: (8)..(8)
<223> OTHER INFORMATION: the amino acid at this position can be an R, H,
      or S
<220> FEATURE:
<221> NAME/KEY: MISC_FEATURE
<222> LOCATION: (10)..(10)
<223> OTHER INFORMATION: the amino acid at this position can be an R or
      P
<220> FEATURE:
<221> NAME/KEY: MISC_FEATURE
<222> LOCATION: (11)..(11)
<223> OTHER INFORMATION: the amino acid at this position can be an L or
      V
<220> FEATURE:
<221> NAME/KEY: MISC_FEATURE
<222> LOCATION: (14)..(14)
<223> OTHER INFORMATION: the amino acid at this position can be an R or
      G
<220> FEATURE:
<221> NAME/KEY: MISC_FEATURE
<222> LOCATION: (15)..(15)
<223> OTHER INFORMATION: the amino acid at this position can be a T or N
<220> FEATURE:
<221> NAME/KEY: MISC_FEATURE
<222> LOCATION: (20)..(20)
<223> OTHER INFORMATION: the amino acid at this position can be a Q or L

<400> SEQUENCE: 14

Xaa Leu Lys Xaa Xaa Xaa Cys Xaa Ser Xaa Xaa Phe Pro Xaa Xaa Trp
1               5                   10                  15

Asp Leu Arg Xaa
            20

<210> SEQ ID NO 15
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 15

Ala Ser Val Thr Phe Asn Leu Phe Arg Leu Leu Thr Arg Asp Leu Lys
1               5                   10                  15

Tyr
```

(Xaa at end of preceding sequence)

```
<210> SEQ ID NO 16
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 16

Ala Ser Val Thr Phe Asn Leu Phe Arg Leu Leu Thr Arg Asp Leu Asn
1               5                   10                  15

Cys

<210> SEQ ID NO 17
<211> LENGTH: 20
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (6)..(6)
<223> OTHER INFORMATION: the amino acid at this position can be a K or
      R
<220> FEATURE:
<221> NAME/KEY: MISC_FEATURE
<222> LOCATION: (8)..(8)
<223> OTHER INFORMATION: the amino acid at this position can be an R or
      H

<400> SEQUENCE: 17

Leu Leu Lys Asp Cys Xaa Cys Xaa Ser Arg Leu Phe Pro Arg Thr Trp
1               5                   10                  15

Asp Leu Arg Gln
            20

<210> SEQ ID NO 18
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 18

Leu Leu Lys Asp Cys Lys Cys Arg Ser Arg Leu Phe Pro Arg Thr Trp
1               5                   10                  15

Asp Leu Arg Gln
            20

<210> SEQ ID NO 19
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 19

Leu Leu Lys Asp Cys Arg Cys His Ser Arg Leu Phe Pro Arg Thr Trp
1               5                   10                  15

Asp Leu Arg Gln
            20

<210> SEQ ID NO 20
<211> LENGTH: 20
<212> TYPE: PRT
<213> ORGANISM: Artificial sequence
```

```
<220> FEATURE:
<223> OTHER INFORMATION: Synthetic amino acid sequence

<400> SEQUENCE: 20

Lys Leu Lys Asn Trp Ser Cys Ser Ser Pro Val Phe Pro Gly Asn Trp
1               5                   10                  15

Asp Leu Arg Leu
            20

<210> SEQ ID NO 21
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 21

Leu Lys Asn Trp Ser Cys Ser Ser Pro Val Phe Pro Gly Asn
1               5                   10

<210> SEQ ID NO 22
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 22

Leu Lys Asp Cys Arg Cys His Ser Arg Leu Phe Pro Arg Thr
1               5                   10

<210> SEQ ID NO 23
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 23

Leu Lys Asp Cys Lys Cys Arg Ser Arg Leu Phe Pro Arg Thr
1               5                   10

<210> SEQ ID NO 24
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 24

Val Ala Tyr Gln Ser Ser Pro Thr Arg Arg Arg Trp Arg Glu Val
1               5                   10                  15

<210> SEQ ID NO 25
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 25

Met Met Cys Leu Lys Lys Gln Asp Leu Tyr Asn Lys Phe Arg Gly
1               5                   10                  15

<210> SEQ ID NO 26
<211> LENGTH: 15
```

```
<212> TYPE: PRT
<213> ORGANISM: Artificial sequence
<220> FEATURE:
<223> OTHER INFORMATION: Synthetic amino acid sequence

<400> SEQUENCE: 26

Ser Glu Tyr Leu Asp Tyr Leu Phe Glu Val Glu Pro Ala Pro Pro
1               5                   10                  15

<210> SEQ ID NO 27
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 27

Asn Ala Thr Tyr Gln Leu Pro Pro Cys Met Pro Pro Leu Asp Leu Lys
1               5                   10                  15

Tyr

<210> SEQ ID NO 28
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 28

Ala Arg Thr Ile Tyr Thr Phe Ser Val Pro Lys Tyr Ser Lys Phe
1               5                   10                  15

<210> SEQ ID NO 29
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 29

Pro Gln Glu Leu Gln Ala Phe Lys Arg Ala Lys Asp Ala Leu Glu Glu
1               5                   10                  15

Ser Leu

<210> SEQ ID NO 30
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 30

Pro Gln Glu Leu Ala Ser Phe Lys Lys Ala Arg Asp Ala Leu Glu Glu
1               5                   10                  15

Ser Leu

<210> SEQ ID NO 31
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 31

Glu Ala Thr Ala Asp Thr Asp Pro Ala Leu Gly Asp Val Leu Asp Gln
```

```
1               5                   10                  15
Pro Leu

<210> SEQ ID NO 32
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 32

Glu Ala Thr Ala Asp Thr Asp Pro Ala Leu Val Asp Val Leu Asp Gln
1               5                   10                  15

Pro Leu

<210> SEQ ID NO 33
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 33

Glu Ala Ala Ala Gly Pro Ala Leu Glu Asp Val Leu Asp Gln Pro Leu
1               5                   10                  15

<210> SEQ ID NO 34
<211> LENGTH: 179
<212> TYPE: PRT
<213> ORGANISM: Homo sapiens

<400> SEQUENCE: 34

Met Arg Pro Ser Val Trp Ala Ala Val Ala Gly Leu Trp Val Leu
1               5                   10                  15

Cys Thr Val Ile Ala Ala Ala Pro Arg Arg Cys Leu Leu Ser His Tyr
                20                  25                  30

Arg Ser Leu Glu Pro Arg Thr Leu Ala Ala Lys Ala Leu Arg Asp
            35                  40                  45

Arg Tyr Glu Glu Glu Ala Leu Ser Trp Gly Gln Arg Asn Cys Ser Phe
    50                  55                  60

Arg Pro Arg Arg Asp Pro Pro Arg Pro Ser Ser Cys Ala Arg Leu Arg
65                  70                  75                  80

His Val Ala Arg Gly Ile Ala Asp Ala Gln Ala Val Leu Ser Gly Leu
                85                  90                  95

His Arg Ser Glu Leu Leu Pro Gly Ala Gly Pro Ile Leu Glu Leu Leu
            100                 105                 110

Ala Ala Ala Gly Arg Asp Val Ala Ala Cys Leu Glu Leu Ala Arg Pro
        115                 120                 125

Gly Ser Ser Arg Lys Val Pro Gly Ala Gln Lys Arg Arg His Lys Pro
    130                 135                 140

Arg Arg Ala Asp Ser Pro Arg Cys Arg Lys Ala Ser Val Val Phe Asn
145                 150                 155                 160

Leu Leu Arg Leu Leu Thr Trp Glu Leu Arg Leu Ala Ala His Ser Gly
                165                 170                 175

Pro Cys Leu

<210> SEQ ID NO 35
<211> LENGTH: 325
<212> TYPE: PRT
```

<213> ORGANISM: Homo sapiens

<400> SEQUENCE: 35

Met Ala Trp Ser Leu Gly Ser Trp Leu Gly Cys Leu Leu Val Ser
1               5                   10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Trp Met Val Ala
210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
            260                 265                 270

Pro His His Asn Thr Leu Leu Phe Phe Ser Phe Pro Leu Ser Asp Glu
        275                 280                 285

Asn Asp Val Phe Asp Lys Leu Ser Val Ile Ala Glu Asp Ser Glu Ser
290                 295                 300

Gly Lys Gln Asn Pro Gly Asp Ser Cys Ser Leu Gly Thr Pro Pro Gly
305                 310                 315                 320

Gln Gly Pro Gln Ser
                325

<210> SEQ ID NO 36
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 36

Glu Cys Asp Phe Ser Ser Leu Ser Lys Tyr Gly Asp His Thr Leu Arg
1               5                   10                  15

Val

<210> SEQ ID NO 37
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 37

Phe Thr Ala Gln Tyr Leu Ser Tyr Arg Ile Phe Gln Asp Lys Cys
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 38

Thr Ala Gln Leu Tyr Ser Tyr Arg Ile Phe Gln Asp Lys Cys Met
1               5                   10                  15

<210> SEQ ID NO 39
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 39

Glu Cys Asp Phe Ser Ser Leu Ser Lys Tyr Gly Asp His Thr Leu Arg
1               5                   10                  15

<210> SEQ ID NO 40
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 40

Gly Met Gln Val Glu Val Leu Ala Asp Cys Leu His Met Arg Phe Leu
1               5                   10                  15

Ala

<210> SEQ ID NO 41
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 41

Gln Val Glu Val Leu Ala Asp Cys Leu His Met Arg Phe Leu Ala Pro
1               5                   10                  15

Lys Ile Glu Asn Glu
            20

<210> SEQ ID NO 42
<211> LENGTH: 14
<212> TYPE: PRT
<213> ORGANISM: Artificial sequence
<220> FEATURE:

```
<223> OTHER INFORMATION: Synthetic amino acid sequence

<400> SEQUENCE: 42

Cys Leu His Met Arg Phe Leu Ala Pro Lys Ile Glu Asn Glu
1               5                   10

<210> SEQ ID NO 43
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 43

Phe Leu Ala Pro Lys Ile Glu Asn Glu Tyr Glu Thr Trp Thr Met
1               5                   10                  15

<210> SEQ ID NO 44
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 44

Trp Thr Val Val Leu Val Thr Leu Val Leu Gly Leu Ala Val Ala Gly
1               5                   10                  15

<210> SEQ ID NO 45
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 45

Val Leu Val Thr Leu Val Leu Gly Leu Ala Val Ala Gly Pro Val Pro
1               5                   10                  15

<210> SEQ ID NO 46
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 46

Thr Leu Val Leu Gly Leu Ala Val Ala Gly Pro Val Pro Thr Ser
1               5                   10                  15

<210> SEQ ID NO 47
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 47

Val Leu Gly Leu Ala Val Ala Gly Pro Val Pro Thr Ser Lys Pro Thr
1               5                   10                  15

<210> SEQ ID NO 48
<211> LENGTH: 18
<212> TYPE: PRT
<213> ORGANISM: Artificial sequence
<220> FEATURE:
<223> OTHER INFORMATION: Synthetic amino acid sequence
```

<400> SEQUENCE: 48

Gly Leu Ala Val Ala Gly Pro Val Pro Thr Ser Lys Pro Thr Thr Thr
1               5                   10                  15

Gly Lys

<210> SEQ ID NO 49
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 49

Ala Val Ala Gly Pro Val Pro Thr Ser Lys Pro Thr Thr Thr Gly Lys
1               5                   10                  15

<210> SEQ ID NO 50
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 50

Ala Gly Pro Val Pro Thr Ser Lys Pro Thr Thr Thr Gly Lys Gly
1               5                   10                  15

<210> SEQ ID NO 51
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 51

Gly Pro Val Pro Thr Ser Lys Pro Thr Thr Thr Gly Lys Gly Cys His
1               5                   10                  15

<210> SEQ ID NO 52
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 52

Thr Ser Lys Pro Thr Thr Thr Gly Lys Gly Cys His Ile Gly
1               5                   10

<210> SEQ ID NO 53
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 53

Ser Lys Pro Thr Thr Thr Gly Lys Gly Cys His Ile Gly Arg Phe Lys
1               5                   10                  15

<210> SEQ ID NO 54
<211> LENGTH: 17
<212> TYPE: PRT
<213> ORGANISM: Artificial sequence
<220> FEATURE:

<223> OTHER INFORMATION: Synthetic amino acid sequence

<400> SEQUENCE: 54

Pro Thr Thr Thr Gly Lys Gly Cys His Ile Gly Arg Phe Lys Ser Leu
1               5                   10                  15
Ser

<210> SEQ ID NO 55
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 55

Thr Thr Thr Gly Lys Gly Cys His Ile Gly Arg Phe Lys Ser Leu Ser
1               5                   10                  15
Pro

<210> SEQ ID NO 56
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 56

Thr Thr Gly Lys Gly Cys His Ile Gly Arg Phe Lys Ser Leu Ser Pro
1               5                   10                  15

<210> SEQ ID NO 57
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 57

Thr Gly Lys Gly Cys His Ile Gly Arg Phe Lys Ser Leu Ser Pro Gln
1               5                   10                  15

<210> SEQ ID NO 58
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 58

Gly Lys Gly Cys His Ile Gly Arg Phe Lys Ser Leu Ser Pro Gln Glu
1               5                   10                  15

<210> SEQ ID NO 59
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 59

Lys Gly Cys His Ile Gly Arg Phe Lys Ser Leu Ser Pro Gln Glu Leu
1               5                   10                  15

<210> SEQ ID NO 60
<211> LENGTH: 17

```
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 60

Lys Gly Cys His Ile Gly Arg Phe Xaa Ser Leu Ser Pro Gln Glu Leu
1               5                   10                  15

Ala

<210> SEQ ID NO 61
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 61

Gly Cys His Ile Gly Arg Phe Lys Ser Leu Ser Pro Gln Glu Leu Ala
1               5                   10                  15

Ser

<210> SEQ ID NO 62
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 62

Cys His Ile Gly Arg Phe Lys Ser Leu Ser Pro Gln Glu Leu Ala Ser
1               5                   10                  15

Phe

<210> SEQ ID NO 63
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 63

His Ile Gly Arg Phe Lys Ser Leu Ser Pro Gln Glu Leu Ala Ser Phe
1               5                   10                  15

Lys

<210> SEQ ID NO 64
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 64

Ile Gly Arg Phe Lys Ser Leu Ser Pro Gln Glu Leu Ala Ser Phe Lys
1               5                   10                  15

Lys

<210> SEQ ID NO 65
<211> LENGTH: 16
```

```
<212> TYPE: PRT
<213> ORGANISM: Artificial sequence
<220> FEATURE:
<223> OTHER INFORMATION: Synthetic amino acid sequence

<400> SEQUENCE: 65

Leu Glu Asp Val Leu Asp Gln Pro Leu His Thr Leu His His Ile Leu
1               5                   10                  15

<210> SEQ ID NO 66
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 66

Asp Val Leu Asp Gln Pro Leu His Thr Leu His His Ile Leu Ser Gln
1               5                   10                  15

<210> SEQ ID NO 67
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 67

Leu Asp Gln Pro Leu His Thr Leu His His Ile Leu Ser Gln Leu Gln
1               5                   10                  15

<210> SEQ ID NO 68
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 68

Gln Pro Leu His Thr Leu His His Ile Leu Ser Gln Leu Gln Ala Cys
1               5                   10                  15

<210> SEQ ID NO 69
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 69

Glu Leu Gln Ala Phe Lys Lys Ala Lys Asp Ala Ile Glu Lys Arg Leu
1               5                   10                  15

Leu Glu

<210> SEQ ID NO 70
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 70

Glu Leu Gln Ala Phe Lys Lys Ala Lys Gly Ala Ile Glu Lys Arg Leu
1               5                   10                  15

Leu Glu
```

```
<210> SEQ ID NO 71
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 71

Asp Ser Val Thr Ser Asn Leu Phe Arg Leu Leu Thr Arg Asp Leu Lys
1               5                   10                  15

Cys

<210> SEQ ID NO 72
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 72

Asp Ser Val Thr Ser Asn Leu Phe Gln Leu Leu Leu Arg Asp Leu Lys
1               5                   10                  15

Cys

<210> SEQ ID NO 73
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 73

Leu Glu Lys Asp Met Arg Cys Ser Ser His Leu Ile Ser Arg Ala Trp
1               5                   10                  15

Asp Leu Lys Gln
            20

<210> SEQ ID NO 74
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 74

Glu Asn Met Thr Asp Ser Ala Leu Ala Thr Ile Leu Gly Gln Pro Leu
1               5                   10                  15

<210> SEQ ID NO 75
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 75

Glu Asn Ile Asn Asp Ser Ala Leu Thr Thr Ile Leu Gly Gln Pro Leu
1               5                   10                  15

<210> SEQ ID NO 76
<211> LENGTH: 18
<212> TYPE: PRT
<213> ORGANISM: Artificial sequence
<220> FEATURE:
<223> OTHER INFORMATION: Synthetic amino acid sequence
```

<400> SEQUENCE: 76

Lys Ala Glu Lys Phe Gln Leu Ile Lys Lys Leu Ala Glu Arg Glu Asp
1               5                   10                  15

Leu Ala

<210> SEQ ID NO 77
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 77

Arg Arg Leu Val Thr Asp Leu Ser Asn Ser Leu Asp Phe Cys Thr Lys
1               5                   10                  15

Leu

<210> SEQ ID NO 78
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 78

Lys Ala Ser Leu Leu Asp Ser Arg Asp Ile Gln Ser Arg His Lys Glu
1               5                   10                  15

Cys Leu Met Trp
            20

<210> SEQ ID NO 79
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 79

Pro Gln Ser Met Ala Thr Leu Gly Glu Leu Ala Ile Leu Asp Thr Asn
1               5                   10                  15

<210> SEQ ID NO 80
<211> LENGTH: 35
<212> TYPE: PRT
<213> ORGANISM: Artificial sequence
<220> FEATURE:
<223> OTHER INFORMATION: Synthetic amino acid sequence

<400> SEQUENCE: 80

Val Gln Ala Ala Ser Ala His Gly Arg Ser Pro Arg Val Glu Ser Arg
1               5                   10                  15

Tyr Leu Glu Tyr Leu Phe Asp Val Glu Leu Ala Pro Pro Thr Leu Val
            20                  25                  30

Leu Thr Gln
        35

<210> SEQ ID NO 81
<211> LENGTH: 41
<212> TYPE: PRT
<213> ORGANISM: Artificial sequence
<220> FEATURE:
<223> OTHER INFORMATION: Synthetic amino acid sequence

<400> SEQUENCE: 81

Leu Phe Pro Asp Thr Pro Tyr Gly Gln Pro Val Gln Ile Pro Leu Gln
1               5                   10                  15

Gln Gly Ala Ser Arg Arg His Cys Leu Ser Ala Arg Thr Val Tyr Thr
            20                  25                  30

Leu Ile Asp Ile Lys Tyr Ser Gln Phe
            35                  40

<210> SEQ ID NO 82
<211> LENGTH: 17
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: the amino acid at this position can be an A or
      D
<220> FEATURE:
<221> NAME/KEY: MISC_FEATURE
<222> LOCATION: (5)..(5)
<223> OTHER INFORMATION: the amino acid at this position can be a S or F
<220> FEATURE:
<221> NAME/KEY: MISC_FEATURE
<222> LOCATION: (9)..(9)
<223> OTHER INFORMATION: the amino acid at this position can be a R or Q
<220> FEATURE:
<221> NAME/KEY: MISC_FEATURE
<222> LOCATION: (16)..(16)
<223> OTHER INFORMATION: the amino acid at this position can be a K or N
<220> FEATURE:
<221> NAME/KEY: MISC_FEATURE
<222> LOCATION: (17)..(17)
<223> OTHER INFORMATION: the amino acid at this position can be a Y or C

<400> SEQUENCE: 82

Xaa Ser Val Thr Xaa Asn Leu Phe Xaa Leu Leu Thr Arg Asp Leu Xaa
1               5                   10                  15

Xaa

<210> SEQ ID NO 83
<211> LENGTH: 10
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The amino acid at this position can be any
      amino acid.
<220> FEATURE:
<221> NAME/KEY: MISC_FEATURE
<222> LOCATION: (10)..(10)
<223> OTHER INFORMATION: The amino acid at this position can be any
      amino acid.

<400> SEQUENCE: 83

Xaa Val Leu Gly Leu Ala Val Ala Gly Xaa
1               5                   10

<210> SEQ ID NO 84
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 84

```
Val Leu Val Thr Leu
1               5

<210> SEQ ID NO 85
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 85

Trp Thr Val Val Leu Val Thr Leu
1               5

<210> SEQ ID NO 86
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 86

Pro Val Pro Thr Ser
1               5

<210> SEQ ID NO 87
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 87

Pro Val Pro Thr Ser Lys Pro Thr
1               5

<210> SEQ ID NO 88
<211> LENGTH: 11
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The amino acid at this position can be any
      amino acid.
<220> FEATURE:
<221> NAME/KEY: MISC_FEATURE
<222> LOCATION: (11)..(11)
<223> OTHER INFORMATION: The amino acid at this position can be any
      amino acid.

<400> SEQUENCE: 88

Xaa Thr Ser Lys Pro Thr Thr Thr Gly Lys Xaa
1               5                   10

<210> SEQ ID NO 89
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 89

Gly Leu Ala Val Ala Gly Pro Val Pro
1               5
```

<210> SEQ ID NO 90
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 90

Ala Val Ala Gly Pro Val Pro
1               5

<210> SEQ ID NO 91
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 91

Ala Gly Pro Val Pro
1               5

<210> SEQ ID NO 92
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 92

Gly Pro Val Pro
1

<210> SEQ ID NO 93
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 93

Gly Cys His Ile Gly
1               5

<210> SEQ ID NO 94
<211> LENGTH: 10
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The amino acid at this position can be any
      amino acid.
<220> FEATURE:
<221> NAME/KEY: MISC_FEATURE
<222> LOCATION: (10)..(10)
<223> OTHER INFORMATION: The amino acid at this position can be any
      amino acid.

<400> SEQUENCE: 94

Xaa Gly Cys His Ile Gly Arg Phe Lys Xaa
1               5                   10

<210> SEQ ID NO 95
<211> LENGTH: 5
<212> TYPE: PRT

```
<213> ORGANISM: Artificial sequence
<220> FEATURE:
<223> OTHER INFORMATION: Synthetic amino acid sequence

<400> SEQUENCE: 95

Thr Thr Thr Gly Lys
1               5

<210> SEQ ID NO 96
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 96

Pro Thr Thr Thr Gly Lys
1               5

<210> SEQ ID NO 97
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 97

Ser Lys Pro Thr Thr Thr Gly Lys
1               5

<210> SEQ ID NO 98
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 98

Ser Leu Ser Pro
1

<210> SEQ ID NO 99
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 99

Ser Leu Ser Pro Gln
1               5

<210> SEQ ID NO 100
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 100

Ser Leu Ser Pro Gln Glu
1               5

<210> SEQ ID NO 101
<211> LENGTH: 7
<212> TYPE: PRT
<213> ORGANISM: Artificial sequence
```

```
<220> FEATURE:
<223> OTHER INFORMATION: Synthetic amino acid sequence

<400> SEQUENCE: 101

Ser Leu Ser Pro Gln Glu Leu
1               5

<210> SEQ ID NO 102
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 102

Ser Leu Ser Pro Gln Glu Leu Ala
1               5

<210> SEQ ID NO 103
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 103

Ser Leu Ser Pro Gln Glu Leu Ala Ser
1               5

<210> SEQ ID NO 104
<211> LENGTH: 12
<212> TYPE: PRT
<213> ORGANISM: Artificial sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: The amino acid at this position can be any
      amino acid.
<220> FEATURE:
<221> NAME/KEY: MISC_FEATURE
<222> LOCATION: (12)..(12)
<223> OTHER INFORMATION: The amino acid at this position can be any
      amino acid.

<400> SEQUENCE: 104

Xaa Gln Pro Leu His Thr Leu His His Ile Leu Xaa
1               5                   10

<210> SEQ ID NO 105
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 105

Asp Val Leu Asp
1

<210> SEQ ID NO 106
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 106
```

```
Leu Glu Asp Val Leu Asp
1               5

<210> SEQ ID NO 107
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 107

Ser Gln Leu Gln
1

<210> SEQ ID NO 108
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 108

Ser Gln Leu Gln Ala Cys
1               5

<210> SEQ ID NO 109
<211> LENGTH: 50
<212> TYPE: PRT
<213> ORGANISM: Artificial Sequence
<220> FEATURE:
<223> OTHER INFORMATION: Synthetic amino acid sequence

<400> SEQUENCE: 109

Lys Gly Gln Cys Thr Phe Thr Ala Gln Tyr Leu Cys Ser Tyr Arg Ile
1               5                   10                  15

Cys Phe Gln Asp Lys Cys Met Gln Thr Thr Leu Thr Glu Cys Asp Phe
                20                  25                  30

Ser Ser Leu Ser Lys Tyr Gly Asp His Thr Leu Arg Val Arg Ala Glu
            35                  40                  45

Cys Ala
    50
```